(12) United States Patent
Holzer et al.

(10) Patent No.: US 10,137,015 B2
(45) Date of Patent: Nov. 27, 2018

(54) KNITTED STENT JACKETS

(75) Inventors: Asher Holzer, Haifa (IL); Eli Bar, Moshav Megadim (IL); Ofir Paz, Rishon-lezion (IL)

(73) Assignee: INSPIREMD LTD., Tel Aviv (IL)

( * ) Notice: Subject to any disclaimer, the term of this patent is extended or adjusted under 35 U.S.C. 154(b) by 56 days.

(21) Appl. No.: 12/445,980

(22) PCT Filed: Oct. 18, 2007

(86) PCT No.: PCT/IL2007/001255
§ 371 (c)(1),
(2), (4) Date: Apr. 17, 2009

(87) PCT Pub. No.: WO2008/047369
PCT Pub. Date: Apr. 24, 2008

(65) Prior Publication Data
US 2010/0324651 A1 Dec. 23, 2010

Related U.S. Application Data

(60) Provisional application No. 60/877,162, filed on Dec. 27, 2006, provisional application No. 60/860,485, (Continued)

(51) Int. Cl.
*A61F 2/07* (2013.01)
*A61F 2/90* (2013.01)
(Continued)

(52) U.S. Cl.
CPC ............... *A61F 2/90* (2013.01); *A61F 2/95* (2013.01); *A61F 2/958* (2013.01);
(Continued)

(58) Field of Classification Search
USPC ... 623/1.12, 1.13, 1.23, 1.32, 1.34, 1.5–1.54
See application file for complete search history.

(56) References Cited

U.S. PATENT DOCUMENTS

| 4,164,045 A | 8/1979 | Bokros et al. |
| 4,300,244 A | 11/1981 | Bokros |

(Continued)

FOREIGN PATENT DOCUMENTS

| CN | 1414840 A | 4/2003 |
| EP | 0839506 A1 | 5/1998 |

(Continued)

OTHER PUBLICATIONS

U.S. Appl. No. 11/582,354 Official Action dated Nov. 4, 2010.
(Continued)

*Primary Examiner* — Leslie Lopez
(74) *Attorney, Agent, or Firm* — Haynes & Boone, LLP

(57) ABSTRACT

Disclosed is an assembly for opening a vessel lumen comprising a radially expandable stent configured to open a vessel lumen, the radially expandable stent comprises a curved wall having a proximal portion, a distal portion and a lumen connecting the proximal portion and the distal portion. The assembly further comprises a knitted jacket comprising a plurality of interconnected loops, the knitted jacket further comprising a tubular wall that substantially surrounds an exterior surface of the radially expandable stent, and at least one retainer belt that slidingly passes through at least one knitted loop of the plurality of interconnected loops in the knitted jacket.

16 Claims, 11 Drawing Sheets

Related U.S. Application Data filed on Nov. 22, 2006, provisional application No. 60/852,392, filed on Oct. 18, 2006.

(51) Int. Cl.
*A61F 2/95* (2013.01)
*A61F 2/958* (2013.01)
*A61F 2/966* (2013.01)

(52) U.S. Cl.
CPC . *A61F 2002/075* (2013.01); *A61F 2002/9511* (2013.01); *A61F 2002/9583* (2013.01); *A61F 2002/9665* (2013.01); *A61F 2220/0075* (2013.01); *A61F 2250/0048* (2013.01)

(56) References Cited

U.S. PATENT DOCUMENTS

| | | | |
|---|---|---|---|
| 4,321,711 A | 3/1982 | Mano | |
| 4,425,908 A | 1/1984 | Simon | |
| 4,655,771 A * | 4/1987 | Wallsten | A61F 2/01 606/198 |
| 4,723,549 A | 2/1988 | Wholey et al. | |
| 4,832,688 A | 5/1989 | Sagae et al. | |
| 4,865,017 A | 9/1989 | Shinozuka | |
| 4,873,978 A | 10/1989 | Ginsburg | |
| 4,969,891 A | 11/1990 | Gewertz | |
| 4,990,156 A | 2/1991 | Lefebvre | |
| 4,998,539 A | 3/1991 | Delsanti | |
| 5,019,090 A | 5/1991 | Pinchuk | |
| 5,122,154 A | 6/1992 | Rhodes | |
| 5,152,777 A | 10/1992 | Goldberg et al. | |
| 5,171,233 A | 12/1992 | Amplatz et al. | |
| 5,192,286 A | 3/1993 | Phan et al. | |
| 5,236,447 A | 8/1993 | Kubo et al. | |
| 5,330,482 A | 7/1994 | Gibbs et al. | |
| 5,366,504 A | 11/1994 | Andersen et al. | |
| 5,382,261 A | 1/1995 | Palmaz | |
| 5,383,887 A | 1/1995 | Nadal | |
| 5,403,341 A | 4/1995 | Solar | |
| 5,421,955 A | 6/1995 | Lau et al. | |
| 5,470,313 A | 11/1995 | Crocker et al. | |
| 5,486,183 A | 1/1996 | Middleman et al. | |
| 5,569,295 A | 10/1996 | Lam | |
| 5,591,228 A | 1/1997 | Edoga | |
| 5,713,948 A | 2/1998 | Uflacker | |
| 5,769,884 A | 6/1998 | Solovay | |
| 5,824,037 A | 10/1998 | Fogarty et al. | |
| 5,827,324 A | 10/1998 | Cassell et al. | |
| 5,833,651 A | 11/1998 | Donovan et al. | |
| 5,843,116 A | 12/1998 | Crocker et al. | |
| 5,843,161 A | 12/1998 | Solovay | |
| 5,871,538 A | 2/1999 | Dereume | |
| 5,908,448 A | 6/1999 | Roberts et al. | |
| 5,919,225 A | 7/1999 | Lau et al. | |
| 5,941,896 A | 8/1999 | Kerr | |
| 5,957,974 A | 9/1999 | Thompson et al. | |
| 5,984,955 A | 11/1999 | Wisselink | |
| 6,007,543 A | 12/1999 | Ellis et al. | |
| 6,015,430 A | 1/2000 | Wall | |
| 6,015,432 A * | 1/2000 | Rakos et al. | 623/1.13 |
| 6,027,517 A | 2/2000 | Crocker et al. | |
| 6,030,414 A | 2/2000 | Taheri | |
| 6,042,597 A | 3/2000 | Kveen et al. | |
| 6,066,167 A | 5/2000 | Lau et al. | |
| 6,077,273 A | 6/2000 | Euteneuer et al. | |
| 6,096,027 A * | 8/2000 | Layne | 606/1 |
| 6,152,144 A | 11/2000 | Lesh et al. | |
| 6,176,875 B1 | 1/2001 | Lenker et al. | |
| 6,245,089 B1 | 6/2001 | Daniel et al. | |
| 6,254,627 B1 | 7/2001 | Freidberg | |
| 6,263,880 B1 | 7/2001 | Parker et al. | |
| 6,306,162 B1 | 10/2001 | Patel | |
| 6,340,364 B2 | 1/2002 | Kanesaka | |
| 6,348,065 B1 | 2/2002 | Brown et al. | |
| 6,357,104 B1 | 3/2002 | Myers | |
| 6,361,558 B1 | 3/2002 | Hieshima et al. | |
| 6,369,039 B1 | 4/2002 | Palasis et al. | |
| 6,371,962 B1 | 4/2002 | Ellis et al. | |
| 6,383,171 B1 | 5/2002 | Gifford et al. | |
| 6,432,129 B2 | 8/2002 | DiCaprio | |
| 6,436,132 B1 | 8/2002 | Patel et al. | |
| 6,447,796 B1 | 9/2002 | Vook et al. | |
| 6,451,051 B2 | 9/2002 | Drasler et al. | |
| 6,461,381 B2 | 10/2002 | Israel et al. | |
| 6,464,722 B2 | 10/2002 | Israel et al. | |
| 6,468,230 B2 | 10/2002 | Muni et al. | |
| 6,488,703 B1 | 12/2002 | Kveen et al. | |
| 6,506,203 B1 | 1/2003 | Boyle et al. | |
| 6,540,773 B2 | 4/2003 | Dong | |
| 6,551,352 B2 * | 4/2003 | Clerc et al. | 623/1.2 |
| 6,554,855 B1 | 4/2003 | Dong | |
| 6,602,285 B1 | 8/2003 | Von Oepen et al. | |
| 6,620,654 B2 | 9/2003 | Salman | |
| 6,641,607 B1 | 11/2003 | Hossainy et al. | |
| 6,645,239 B1 | 11/2003 | Park et al. | |
| 6,669,717 B2 | 12/2003 | Marotta et al. | |
| 6,669,961 B2 | 12/2003 | Kim et al. | |
| 6,673,814 B2 | 1/2004 | Joshi et al. | |
| 6,676,695 B2 * | 1/2004 | Solem | 623/1.12 |
| 6,682,554 B2 | 1/2004 | Oepen et al. | |
| 6,702,849 B1 | 3/2004 | Dutta et al. | |
| 6,712,834 B2 | 3/2004 | Yassour et al. | |
| 6,712,842 B1 | 3/2004 | Gifford, III et al. | |
| 6,755,856 B2 | 6/2004 | Fierens et al. | |
| 6,802,851 B2 | 10/2004 | Jones et al. | |
| 6,808,533 B1 | 10/2004 | Goodwin et al. | |
| 6,818,014 B2 | 11/2004 | Brown et al. | |
| 6,827,731 B2 | 12/2004 | Armstrong et al. | |
| 6,835,189 B2 | 12/2004 | Musbach et al. | |
| 6,893,457 B2 | 5/2005 | Dong | |
| 6,902,522 B1 | 6/2005 | Walsh et al. | |
| 6,918,920 B1 | 7/2005 | Wang et al. | |
| 6,919,100 B2 | 7/2005 | Narayanan | |
| 6,929,658 B1 | 8/2005 | Freidberg et al. | |
| 6,932,832 B2 | 8/2005 | Patel et al. | |
| 6,939,374 B2 | 9/2005 | Banik et al. | |
| 6,939,376 B2 | 9/2005 | Shulze et al. | |
| 6,953,476 B1 | 10/2005 | Shalev | |
| 6,981,986 B1 | 1/2006 | Brown et al. | |
| 6,997,946 B2 | 2/2006 | Girton et al. | |
| 7,011,676 B2 | 3/2006 | Dong | |
| 7,037,330 B1 | 5/2006 | Rivelli, Jr. et al. | |
| 7,041,129 B2 | 5/2006 | Rourke et al. | |
| 7,083,644 B1 * | 8/2006 | Moroni | 623/1.51 |
| 7,198,638 B2 | 4/2007 | Dong | |
| 7,491,225 B2 | 2/2009 | Weber et al. | |
| 7,722,634 B2 | 5/2010 | Panetta et al. | |
| 7,996,993 B2 | 8/2011 | Gray et al. | |
| 8,097,015 B2 | 1/2012 | Devellian | |
| 2002/0022860 A1 | 2/2002 | Borillo et al. | |
| 2002/0045917 A1 | 4/2002 | Ambrisco et al. | |
| 2002/0082685 A1 | 6/2002 | Sirhan et al. | |
| 2002/0111668 A1 | 8/2002 | Smith | |
| 2002/0128679 A1 | 9/2002 | Turovskiy et al. | |
| 2002/0143387 A1 * | 10/2002 | Soetikno et al. | 623/1.15 |
| 2002/0161393 A1 | 10/2002 | Demond et al. | |
| 2003/0028239 A1 | 2/2003 | Dong | |
| 2003/0055452 A1 | 3/2003 | Joergensen et al. | |
| 2003/0093112 A1 | 5/2003 | Addis | |
| 2003/0100945 A1 | 5/2003 | Yodfat et al. | |
| 2003/0130718 A1 | 7/2003 | Palmas et al. | |
| 2003/0149464 A1 | 8/2003 | Dong | |
| 2003/0176884 A1 | 9/2003 | Berrada et al. | |
| 2003/0229389 A1 * | 12/2003 | Escano | 623/1.13 |
| 2004/0030377 A1 | 2/2004 | Dubson et al. | |
| 2004/0044395 A1 * | 3/2004 | Nelson | 623/1.12 |
| 2004/0054402 A1 * | 3/2004 | DiCarlo | 623/1.23 |
| 2004/0068314 A1 | 4/2004 | Jones et al. | |
| 2004/0111142 A1 | 6/2004 | Rourke et al. | |
| 2004/0116960 A1 | 6/2004 | Demond et al. | |
| 2004/0143272 A1 * | 7/2004 | Cully et al. | 606/108 |
| 2004/0158312 A1 | 8/2004 | Chouinard et al. | |
| 2004/0225322 A1 | 11/2004 | Garrison et al. | |
| 2004/0236407 A1 * | 11/2004 | Fierens et al. | 623/1.16 |

(56) References Cited

U.S. PATENT DOCUMENTS

| | | | |
|---|---|---|---|
| 2004/0267347 A1 | 12/2004 | Cervantes | |
| 2004/0267352 A1 | 12/2004 | Davidson | |
| 2005/0038503 A1 | 2/2005 | Greenhalgh et al. | |
| 2005/0049680 A1 | 3/2005 | Fischell et al. | |
| 2005/0110214 A1 | 5/2005 | Shank et al. | |
| 2005/0119688 A1 | 6/2005 | Bergheim | |
| 2005/0152938 A1* | 7/2005 | Williams et al. | 424/423 |
| 2005/0159803 A1 | 7/2005 | Lad et al. | |
| 2005/0165470 A1* | 7/2005 | Weber | A61F 2/88 623/1.15 |
| 2005/0171591 A1 | 8/2005 | McHale et al. | |
| 2005/0182473 A1 | 8/2005 | Eidenschink et al. | |
| 2005/0187140 A1 | 8/2005 | Hunter et al. | |
| 2005/0197690 A1 | 9/2005 | Molaei et al. | |
| 2005/0222607 A1 | 10/2005 | Palmer et al. | |
| 2005/0277976 A1 | 12/2005 | Galdonik et al. | |
| 2006/0009835 A1 | 1/2006 | Osborne et al. | |
| 2006/0085064 A1 | 4/2006 | Tuch | |
| 2006/0116748 A1 | 6/2006 | Kaplan et al. | |
| 2006/0155359 A1 | 7/2006 | Watson | |
| 2006/0175727 A1 | 8/2006 | Fierens et al. | |
| 2006/0259131 A1 | 11/2006 | Molaei et al. | |
| 2006/0259137 A1 | 11/2006 | Artof et al. | |
| 2006/0276887 A1* | 12/2006 | Brady et al. | 623/1.53 |
| 2007/0043428 A1 | 2/2007 | Jennings et al. | |
| 2007/0135890 A1 | 6/2007 | Dong | |
| 2007/0179593 A1 | 8/2007 | Fierens et al. | |
| 2007/0179601 A1 | 8/2007 | Fierens et al. | |
| 2007/0208374 A1 | 9/2007 | Boyle et al. | |
| 2007/0213800 A1 | 9/2007 | Fierens et al. | |
| 2007/0270902 A1 | 11/2007 | Slazas et al. | |
| 2007/0276468 A1 | 11/2007 | Holzer et al. | |
| 2008/0023346 A1 | 1/2008 | Vonderwalde | |
| 2008/0172082 A1 | 7/2008 | Holzer et al. | |
| 2009/0012598 A1 | 1/2009 | Abbate et al. | |
| 2009/0138070 A1 | 5/2009 | Holzer et al. | |
| 2009/0248133 A1 | 10/2009 | Bloom et al. | |
| 2010/0056907 A1 | 3/2010 | Rappaport et al. | |
| 2010/0204772 A1 | 8/2010 | Holzer et al. | |
| 2010/0222805 A1 | 9/2010 | Pal et al. | |
| 2010/0241214 A1 | 9/2010 | Holzer et al. | |
| 2011/0098739 A1 | 4/2011 | Bates | |

FOREIGN PATENT DOCUMENTS

| | | | |
|---|---|---|---|
| WO | 8809683 A1 | 12/1988 | |
| WO | 9929262 A1 | 6/1999 | |
| WO | WO 99/53865 | 10/1999 | |
| WO | 0130266 A1 | 5/2001 | |
| WO | 03022325 A2 | 3/2003 | |
| WO | 2003018079 A1 | 3/2003 | |
| WO | 2006010130 A1 | 1/2006 | |
| WO | 2006116636 A1 | 11/2006 | |
| WO | 2006126182 A2 | 11/2006 | |
| WO | 2007067451 A2 | 6/2007 | |
| WO | 2008047367 A2 | 4/2008 | |
| WO | 2008047368 A2 | 4/2008 | |
| WO | 2008047369 A2 | 4/2008 | |
| WO | 2008062414 A2 | 5/2008 | |

OTHER PUBLICATIONS

U.S. Appl. No. 12/445,968 Official Action dated Jan. 25, 2011.
Haj et al., "Acquired Haemophilia A May be Associated with Clopidogrel", British Medical Journal, vol. 329, p. 323, Aug. 7, 2004.
Zakarija et al., "Clopidogrel-Associated TTP: An Update of Pharmacovigilance Efforts Conducted by Independent Researchers, Pharmaceutical Suppliers, and the Food and Drug Administration", STROKE—Journal of American Heart Association, vol. 35, pp. 533-537, Jan. 5, 2004.
Liistro et al., "Late Acute Thrombosis After Paclitaxel Eluting Stent Implantation", Heart Medical Journal, vol. 86, pp. 262-264, Sep. 2001.
Nguyen et al.,"Resistance to Clopidogrel: A Review of The Evidence", Journal of the American College of Cardiology, vol. 45, No. 8, pp. 1157-1164, Apr. 19, 2005.
Fayad et al., "Clinical Imaging of the High-Risk or Vulnerable Atherosclerotic Plaque", American Heart Association, Circulation Research, vol. 89, pp. 305-316, Aug. 17, 2001.
Holzer et al., U.S. Appl. No. 12/445,968 "Bifurcated stent assemblies" filed Apr. 17, 2009.
International Patent Application PCT/IL07/01442 Search Report dated Aug. 27, 2008.
International Patent Application PCT/IL07/01253 Search report dated Jun. 13, 2008.
International Patent Application PCT/IL07/01254 Search Report dated Sep. 30, 2008.
International Patent Application PCT/IL07/01255 Search Report dated Sep. 25, 2008.
U.S. Appl. No. 11/582,354 Official Action dated Jun. 14, 2010.
U.S. Appl. No. 11/797,168 Official Action dated Feb. 23, 2009.
U.S. Appl. No. 11/797,168 Official Action dated Nov. 17, 2009.
U.S. Appl. No. 11/920,972 Official Action dated Mar. 31, 2011.
Israel Patent Application # 198189 Official Action dated Jun. 1, 2011.
Israel Patent Application # 187516 Official Action dated Apr. 14, 2011.
Israel Patent Application # 198190 Official Action dated Jun. 1, 2011.
Israel Patent Application # 198665 Official Action dated Jun. 1, 2011.
U.S. Appl. No. 12/445,968 Official Action dated Jun. 17, 2011.
Chinese Patent Application # 200780046697.4 Official Action dated Apr. 6, 2011.
Chinese Patent Application # 200780046676.2 Office Action dated Apr. 28, 2011.
U.S. Appl. No. 12/445,972 Office Action dated Aug. 22, 2011.
Chinese Patent Application # 200780046659.9 Office Action dated May 11, 2011.
European Patent Application # 07827415.6 Search report dated Feb. 13, 2013.
European Patent Application # 07827227.5 Search report dated Feb. 25, 2013.
U.S. Appl. No. 11/920,972 Office action dated Apr. 16, 2013.
European Patent Application # 07827228.3 Search report dated Mar. 8, 2013.
Israeli Patent Application # 198665 Office action dated Apr. 25, 2013.
International Application PCT/IB2011/055758 Search Report dated May 14, 2012.
U.S. Appl. No. 12/791,008 Official Action dated Mar. 26, 2012.
U.S. Appl. No. 12/445,972 Official Action dated Jun. 18, 2012.
U.S. Appl. No. 12/445,972 Official Action dated Mar. 26, 2012.
Israel Patent Application # 198188 Official Action dated Apr. 16, 2012.
Chinese Patent Application # 200780043259.2 Official Action dated Mar. 31, 2012.
Chinese Patent Application # 200780046697.4 Official Action dated Mar. 23, 2012.
U.S. Appl. No. 11/920,972 Official Action dated Nov. 30, 2011.
U.S. Appl. No. 11/920,972 Advisory Action dated Feb. 10, 2012.
U.S. Appl. No. 12/791,008 Office action dated Oct. 4, 2012.
U.S. Appl. No. 11/920,972 Office action dated Oct. 9, 2012.
IL Patent Application # 198,190 Office action dated Nov. 22, 2012.
EPO, "Supplementary Partial European Search Report," dated Jul. 7, 2004, 4 pages.

* cited by examiner

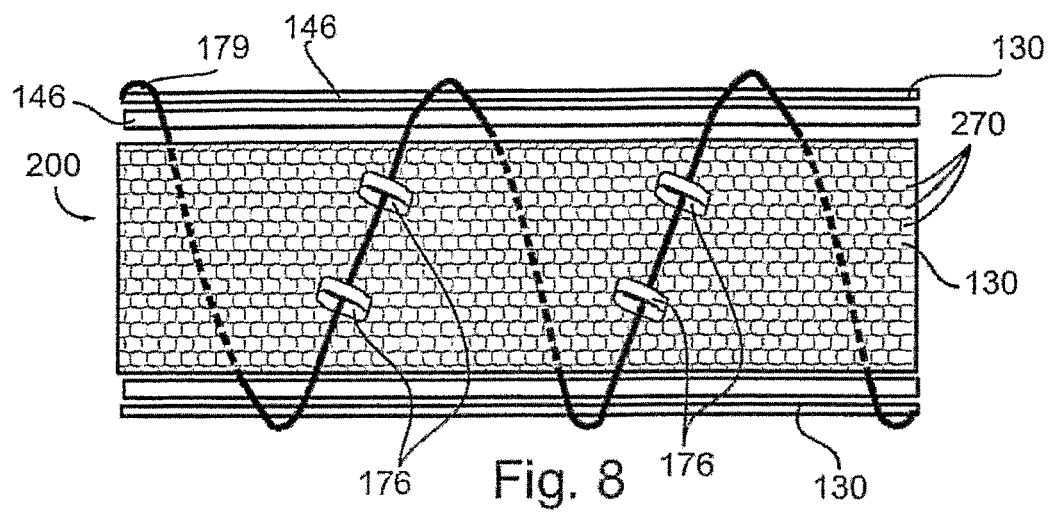
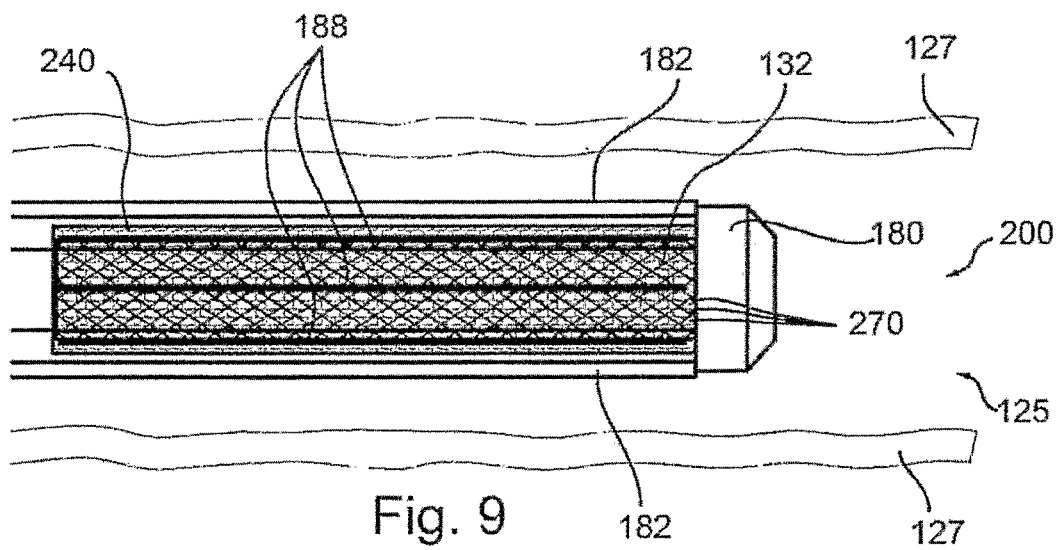
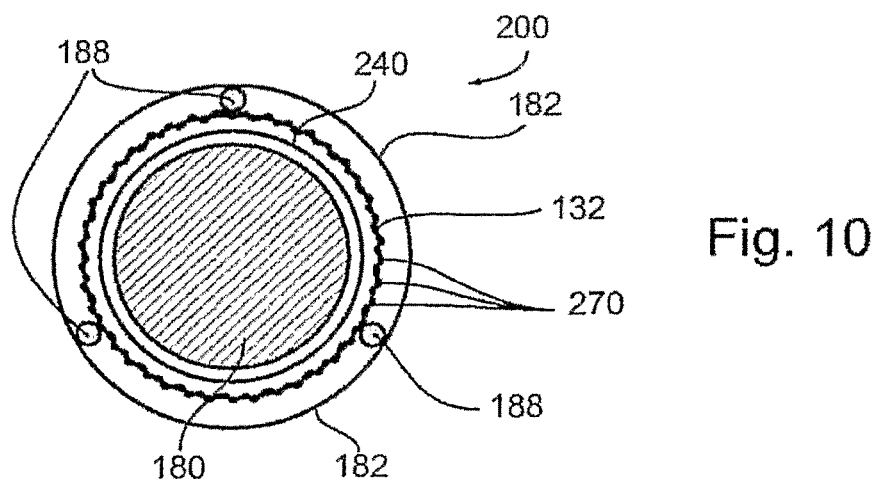

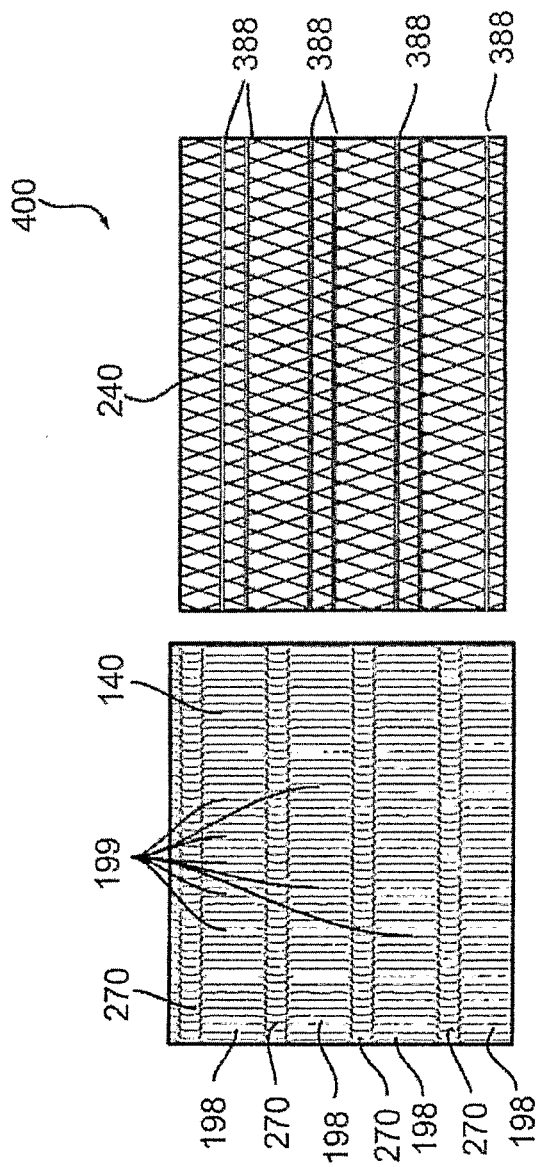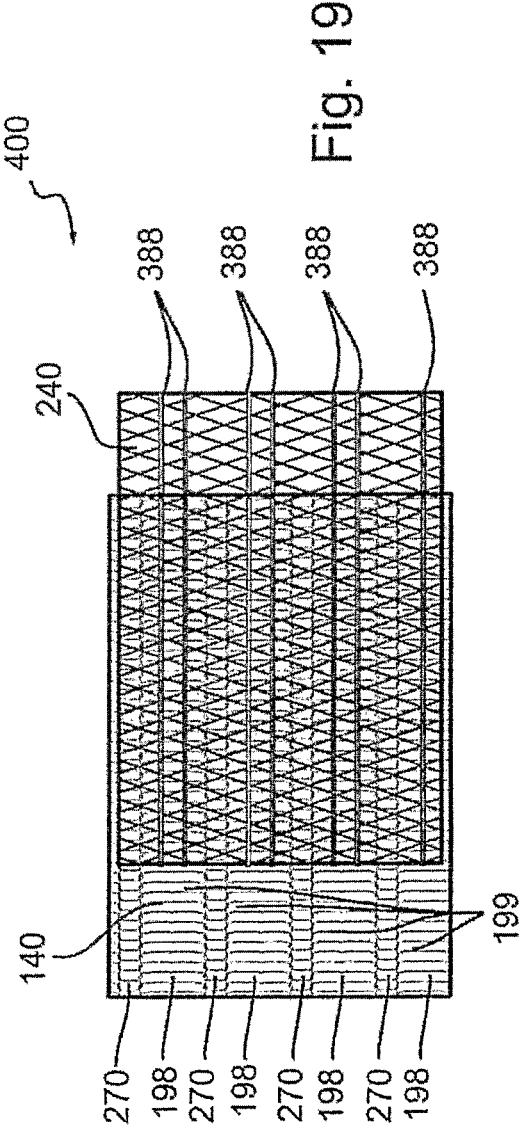

KNITTED STENT JACKETS

RELATED APPLICATIONS

This application is a U.S. National Stage Application of PCT/IL2007/001255, filed Oct. 18, 2017, which claims the benefit of U.S. Provisional Application No. 60/852,392, filed Oct. 18, 2006, U.S. Provisional Application No. 60/860,485, filed Nov. 22, 2006, and U.S. Provisional Application No. 60/877,162, filed Dec. 27, 2006, the disclosure of each of which is hereby incorporated herein by reference.

FIELD AND BACKGROUND OF THE INVENTION

The present invention, in some embodiments thereof, relates to stents and stent jacket assemblies and, more specifically but not exclusively, to low bulk stent jackets designed to resist damage during stent expansion while providing protection against embolitic debris release into the general circulation.

The use of stents to prevent restenosis in treated stenotic vasculature began in 1994 following U.S. Food and Drug Administration approval of the Palmaz-Schatz stent.

Stents made of elastic and/or plastic materials are typically expanded by inflating a balloon within the contracted stent. After stent expansion, the balloon is deflated and removed from the vasculature, leaving the stent in place. Stents containing superelastic materials, for example nitinol, are passed through the vasculature enclosed within a sheath that is retracted to allow stent release and simultaneous expansion.

While stents have resulted in improved long-term blood flow, stents are associated with severe problems during and immediately following stent placement. Stents generate debris from stenotic tissue that enter the general circulation and travel to vital organs, for example the brain and/or lungs, causing vascular blockage, tissue necrosis and/or patient death. Debris generation is endemic to all stents including stents used in chronic heart conditions, carotid arteries, degenerated saphenous vein grafts, and in thrombotic lesions associated with acute coronary syndromes.

The association between stents and life-threatening debris is related to both the vascular environment and stent architecture. The stenotic vessel where the stent is deployed is generally lined with relatively brittle plaques. A conventional stent is typically constructed from a relatively stiff material having large mesh-like apertures that scrape against the surrounding vessel as the stent contracts longitudinally during expansion.

Plaque portions that protrude through the stent apertures are subjected to shear forces and rip loose, creating debris that pass through the stent lumen and into the general circulation.

To reduce the amount of debris entering the circulation, stents are often deployed in conjunction with stent jackets made of a material having small apertures. Stent jackets are typically formed by a process including, inter alia interlocked knitting, braiding, interlacing, and/or dipping a porous mold into one or more reagents.

Jacketed stents in general pose a problem in that the coefficient of expansion of the jacket is typically different from the coefficient of expansion of the associated stent. A jacket located on the outside of the stent, where the jacket provides the greatest protection against debris, must be secured to the stent to maintain proper alignment during stent deployment. The difficulty of securing a jacket with a first coefficient of expansion to a stent having a second coefficient of expansion substantially prevents locating a jacket external to the stent.

SUMMARY OF THE INVENTION

There is thus provided a single fiber knitted stent jacket that that surrounds an external surface of a radial expandable stent and protected from runs with a retainer belt. The retainer belt slidingly passes through key loops, for example at an end of the jacket, so that when the key loops are pulled, an associated retainer belt prevents a run from developing.

In other embodiments, the retainer belt is passed over selected loops to develop planned runs to develop in the jacket during expansion. The planned runs allow the stent jacket to expand while preserving on the bulk of material required for the expansion.

In embodiments, to prevent the run fibers from passing through apertures in the stent into the blood vessel lumen, thereby creating unwanted blood turbulence, longitudinally running fibers are included along the route of the planned run over the stent apertures to keep the fibers external to the lumen.

To protect the jacket from damage due to its different expansion coefficient from that of the stent, the knitted stent jacket is slidingly secured to the stent so that the jacket expands independently of the stent.

According to one aspect of the invention, there is provided an assembly for opening a vessel lumen comprising a radially expandable stent configured to open a vessel lumen, the radially expandable stent comprises a curved wall having a proximal portion, a distal portion and a lumen connecting the proximal portion and the distal portion.

The assembly further comprises a knitted jacket comprising a plurality of interconnected loops, the knitted jacket further comprising a tubular wall that substantially surrounds an exterior surface of the radially expandable stent.

The assembly further includes at least one retainer belt that slidingly passes through at least one knitted loop of the plurality of interconnected loops in the knitted jacket.

In embodiments, at least a portion of the knitted jacket is knitted from a single fiber.

In embodiments, at least a portion of the knitted jacket is knitted from a single fiber comprising multiple filaments.

In embodiments, the at least one retainer belt includes at least one circumferential portion that passes circumferentially around the radially expandable stent.

In embodiments, the at least one retainer belt includes at least one folded retainer belt portion comprising a retainer belt fold that extends into the lumen of the radially expandable stent.

In embodiments, the at least one folded retainer belt portion is operatively associated with an inner wall of the radially expandable stent when the radially expandable stent is in a contracted configuration.

In embodiments, the stent comprises a self-expanding stent. In embodiments, the assembly includes a portion of a catheter aligned with the lumen of the self expanding stent such that the one folded retainer belt portion is pressed between the curved wall of the self expanding stent and the portion of the catheter.

In embodiments, the assembly is configured such that as the knitted jacket expands, a portion of the at least one folded retainer belt portion is pulled free of the operative association with the inner portion of the curved wall. In embodiments, following expansion of the knitted jacket, the at least one folded retainer belt portion circumferentially encircles at least a portion of the self-expanding stent.

In embodiments, the assembly includes a balloon catheter having an inflatable tip substantially aligned with the lumen of the radially expandable stent such that upon inflation the balloon tip causes the radially expandable stent to expand radially outward.

In embodiments, the assembly is configured such that when the radially expandable stent is in a contracted configuration, the balloon is configured to press the at least one folded retainer belt portion against an inner portion of the curved wall of the radially expandable stent.

In embodiments, as the knitted jacket expands, a portion of the at least one folded retainer belt portion is pulled free of the operative association with the inner portion of the curved wall.

In embodiments, following expansion of the knitted jacket, the at least one folded retainer belt portion circumferentially encircles at least a portion of the radially expandable stent.

In embodiments, at least a portion of the at least one retainer belt comprises an elastomeric material.

In embodiments, the at least one retainer belt passes through at least one of the plurality of interconnected loops at the proximal portion of the knitted jacket.

In embodiments, the at least one retainer belt passes through at least one of the plurality of interconnected loops at the distal portion of the knitted jacket.

In embodiments, the at least one retainer belt passes through at least one of the plurality of interconnected loops at an intermediate position between the proximal portion and the distal portion of the knitted jacket.

In embodiments, the at least one retainer belt comprises a proximal retainer belt portion, a distal retainer belt portion, and a central retainer belt portion therebetween. The at least one retainer belt proximal portion is connected to the knitted jacket proximal portion, and the at least one retainer belt distal portion being connected to the knitted jacket distal portion.

In embodiments, the at least one folded retainer belt portion is located along a portion of the central retainer belt portion.

In embodiments, including at least one restrictor operatively associated with the at least one folded retainer belt portion, the at least one folded retainer belt portion is maintained in a folded configuration by the at least one restrictor In embodiments, the at least one restrictor is slidingly attached to the at least one folded retainer belt portion.

In embodiments, the at least one restrictor is from the group of restrictors comprising an adhesive, a band, a ring, a staple, and a stitch.

In embodiments, the assembly is configured such that as the radially expandable stent expands, the at least one folded retainer belt portion is pulled out of the operative association with the at least one restrictor.

In embodiments, the assembly is configured such that when the radially expandable stent is in an expanded configuration, the retainer belt forms a helical shape substantially surrounding the knitted jacket.

In embodiments, at least a portion of the at least one retainer belt comprises an elastomeric material.

In embodiments, the assembly includes a balloon catheter having an inflatable tip operatively associated with the lumen of the radially expandable stent such that upon inflation the balloon tip causes the radially expandable stent to expand radially outward.

In embodiments, the plurality of interconnected loops comprises at least three interconnected loops, at least one first loop, at least one second loop and at least one third loop.

In embodiments, the at least three interconnected loops are located at an end portion of the knitted jacket.

In embodiments, the at least one retainer belt includes at least one portion woven through the at least one first loop, passes around the at least one second loop and through the at least one third loop.

In embodiments, during expansion of the radially expandable stent, the at least one second loop is configured to create a substantially longitudinal run in the knitted jacket.

In embodiments, the assembly further comprises at least one run support configured to operatively associate with the created run and prevent at least a portion of the single fiber from entering the lumen of the radially expandable stent.

In embodiments, the at least one run support comprises at least one cord extending substantially parallel to a longitudinal axis of the radially expandable stent.

In embodiments, the at least one cord is operatively associated with an external surface of the radially expandable stent.

In embodiments, the at least one cord includes a proximal portion attached to a proximal portion of the knitted jacket.

In embodiments, the at least one cord includes a distal portion attached to a distal portion of the knitted jacket.

In embodiments, the at least one cord includes a central portion attached to a central portion of the knitted jacket.

In embodiments, the at least one run support comprises at least one rail attached to the radially expandable stent.

In embodiments, the radially expandable stent comprises a self-expanding stent.

In embodiments, the assembly includes at least one knitted jacket buffering element operatively associated with the knitted jacket.

In embodiments, the at least one jacket buffering element is substantially parallel to a longitudinal axis of the lumen of the radially expandable stent.

In embodiments, the radially expandable stent is moveably set within a compression sheath.

In embodiments, the at least one jacket buffering element extends along an external surface of the knitted jacket and is configured to buffer the knitted jacket from movements of the compression sheath.

In embodiments, the at least one jacket buffering element is attached to a portion of an outer surface of the knitted jacket.

In embodiments, the at least one jacket buffering element comprises at least one cord.

In embodiments, the at least one cord includes a proximal portion attached to a proximal portion of the knitted jacket.

In embodiments, the at least one cord includes a distal portion attached to a distal portion of the knitted jacket.

In embodiments, the at least one cord includes a central portion attached to a central portion of the knitted jacket.

In embodiments, the at least one jacket buffering element extends along an internal surface of the knitted jacket and is configured to buffer the knitted jacket from movement of the radially expandable stent.

In embodiments, the radially expandable stent is moveably set within a compression sheath.

In embodiments, the at least one jacket buffering element comprises at least one extension of the compression sheath, the at least one extension being positioned between at least a portion of the knitted jacket and at least a portion of the radially expandable stent.

In embodiments, the at least one jacket buffering element comprises a curved wall substantially parallel to the outer surface of the compression sheath and extends from an internal portion of the compression sheath.

In embodiments, the compression sheath compresses at least a portion of the radially expandable stent against a stent holding apparatus.

In embodiments, the compression sheath is moved proximally with respect to the radially expandable stent during expansion of the radially expandable stent.

According to another aspect of the invention, there is provided a method for manufacturing a radially expandable stent having a knitted jacket slidably attachable thereto, the method comprising providing a radially expandable stent, locating an expandable balloon inside the expandable stent, operatively associating a knitted tubular jacket with the stent, the knitted tubular jacket comprising at least two knitted end portion loops, and passing a retainer belt through the at least two knitted end portion loops.

The method further comprises forming a folded retainer belt portion in the retainer belt between the at least two knitted end portion loops, positioning said folded retainer belt portion between a portion of a catheter and said stent, and retaining said positioning of said folded retainer belt portion by a radial outward pressure of said portion of said catheter against said stent.

In embodiments, the radially expandable stent comprises a self-expanding stent.

In embodiments, the operatively associating of the knitted tubular jacket comprises locating the knitted tubular jacket external to the stent.

In embodiments, at least a portion of the knitted jacket is knitted from a single fiber.

In embodiments, at least a portion of the knitted jacket is knitted from a single fiber comprising multiple filaments.

According to a further aspect of the invention, there is provided an assembly for opening a vessel lumen comprising a radially expandable stent configured to open a vessel lumen, the radially expandable stent comprising a curved wall having a proximal portion, a distal portion and a lumen connecting the proximal portion and the distal portion, a stent jacket comprising a tubular wall that substantially surrounds the exterior surface of the radially expandable stent and at least one buffering element operatively associated with the jacket.

In embodiments, the at least one buffering element is substantially parallel to a longitudinal axis of the lumen of the radially expandable stent.

In embodiments, the radially expandable stent is moveably set within a compression sheath.

In embodiments, the at least one buffering element extends along an external surface of the stent jacket and is configured to buffer the stent jacket from movements of the compression sheath.

In embodiments, the at least one buffering element is attached to a portion of an outer surface of the stent jacket.

In embodiments, the at least one buffering element comprises at least one cord.

In embodiments, the at least one cord includes a proximal portion attached to a proximal portion of the stent jacket.

In embodiments, the at least one cord includes a distal portion attached to a distal portion of the stent jacket.

In embodiments, the at least one cord includes a central portion attached to a central portion of the stent jacket.

In embodiments, the radially expandable stent is moveably set within a compression sheath.

In embodiments, the stent jacket comprises a material manufactured by a process from the group consisting of interlacing knitting, interlocked knitting, braiding, interlacing, and/or dipping a porous mold into one or more reagents.

In embodiments, the stent jacket comprises an elastomeric material.

In embodiments, the elastomeric material comprises a rubber.

In embodiments, at least a portion of the knitted jacket is knitted from a single fiber.

In embodiments, at least a portion of the knitted jacket is knitted from a fiber made of multi filaments.

In embodiments, the at least one buffering element extends along an internal surface of the stent jacket and is configured to buffer the stent jacket from movements of the radially expandable stent.

In embodiments, the radially expandable stent is moveably set within a compression sheath and the at least one buffering element comprises a curved wall substantially parallel to an outer surface of the compression sheath.

In embodiments, the compression sheath and the at least one buffering element are moved proximally with respect to the radially expandable stent during expansion of the radially expandable stent.

In embodiments, the at least one buffering element comprises at least one extension of the compression sheath, the at least one extension being positioned between at least a portion of the stent jacket and at least a portion of the radially expandable stent.

In embodiments, the at least one buffering element compresses at least a portion of the radially expandable stent against a stent holding apparatus.

In embodiments, the stent jacket comprises a material manufactured by a process from the group of processes consisting of interlacing knitting, interlocked knitting, braiding, interlacing, and/or dipping a porous mold into one or more reagents.

In embodiments, at least a portion of the knitted jacket is knitted from a single fiber.

In embodiments, at least a portion of the knitted jacket is knitted from a single fiber comprising multiple filaments.

In embodiments, the stent jacket comprises an elastomeric material.

In embodiments, the elastomeric material comprises a rubber.

According to still another aspect of the invention, there is provided an assembly for opening a vessel lumen comprising a radially expandable stent configured to open a vessel lumen, the radially expandable stent comprising a curved wall having a proximal portion, a distal portion and a lumen connecting the proximal portion and the distal portion, the radially expandable stent being moveably set within a compression sheath.

The assembly further comprises a knitted jacket comprising a tubular wall that substantially surrounds an exterior surface of the radially expandable stent, the knitted jacket comprising at least three interconnected loops, at least one first loop, at least one second loop and at least one third loop.

The assembly further comprises at least one retainer belt having at least one portion woven through the at least one first loop, around the at least one second loop and through the at least one third loop, the at least one second loop configured to create a run in the knitted jacket upon expansion of the radially expandable stent.

In embodiments, at least a portion of the knitted jacket is knitted from a single fiber.

In embodiments, at least a portion of said knitted jacket is knitted from a single fiber comprising multiple filaments.

In embodiments, the at least three interconnected loops are located at an end portion of the knitted jacket.

In embodiments, the assembly further comprises at least one run support configured to operatively associate with the created run and prevent at least a portion of the fiber from entering the lumen of the radially expandable stent.

In embodiments, the at least one run support comprises at least one cord extending along an external surface of the stent.

In embodiments, the at least one cord is operatively associated with an external surface of the radially expandable stent.

In embodiments, the at least one cord includes a proximal portion attached to a proximal portion of the knitted jacket.

In embodiments, the at least one cord includes a distal portion attached to a distal portion of the knitted jacket.

In embodiments, the at least one cord includes a central portion attached to a central portion of the knitted jacket.

In embodiments, the at least one run support comprises at least one rail attached to the radially expandable stent.

According to still a further aspect of the invention, there is provided a method for causing a controlled run to form in at least a portion of a stent jacket during radial stent expansion, the method comprising: providing a radially expandable stent, knitting a tubular jacket comprising at least three knitted end portion loops, at least one first loop, at least one second loop and at least one third loop, and operatively associating the knitted tubular jacket with the stent.

The method further comprises weaving a retainer belt through the at least one first loop, past the at least one second loop and through the at least one third loop, expanding the radially expandable stent, and forming at least one controlled stent run in a portion of said knitted jacket associated with said at least one second loop.

In embodiments the method includes operatively associating at least one support element with the at least one second loop. In embodiments the method includes operatively associating at least one support element with the knitted tubular jacket.

In embodiments, the at least one support element comprises at least one support cord. In embodiments the method includes operatively associating the at least one cord with an external surface of the radially expandable stent. In embodiments the at least one support element comprises at least one support rail. In embodiments the method includes, operatively associating the one support rail with the radially expandable stent.

According to yet another aspect of the invention, there is provided a method for protecting a jacket on a stent during stent expansion, the method comprising: providing a radially expandable stent, operatively associating a tubular jacket with the stent, and operatively associating at least one buffering element with the jacket.

In embodiments, the at least one buffering element is configured to buffer the stent jacket from movements of the radially expandable stent. In embodiments, the at least one buffering element comprises at least one cord.

In embodiments, the at least one buffering element is configured to buffer the stent jacket from movements of a compression sheath. In embodiments, the at least one buffering element comprises at least one extension of the compression sheath. In embodiments, the at least one extension is positioned between at least a portion of the stent jacket and at least a portion of the radially expandable stent. In embodiments, the at least one buffering element compresses at least a portion of the radially expandable stent against a stent holding apparatus.

According to a still further aspect of the invention, there is provided an assembly for opening a vessel lumen comprising: a radially expandable stent configured to open a vessel lumen, the radially expandable stent comprising a curved wall having a proximal portion, a distal portion, and a lumen connecting the proximal portion and the distal portion; and a stent jacket comprising a tubular wall that substantially surrounds an exterior surface of the radially expandable stent. The assembly further comprises a compression sheath in which the radially expandable stent is moveably set, the compression sheath includes at least one radiopaque marker.

In embodiments, the at least one radiopaque marker is located on a distal portion of the compression sheath.

In embodiments, the at least one radiopaque marker is located proximally to a distal portion of the compression sheath.

In embodiments, at least one radiopaque marker is included on the stent jacket.

In embodiments, the at least one radiopaque marker is located on a proximal portion of the stent jacket.

In embodiments, the at least one radiopaque marker is offset distally from a proximal portion of the stent jacket.

In embodiments, the at least one radiopaque marker is located on a distal portion of the stent jacket.

In embodiments, the at least one radiopaque marker is offset proximally from a distal portion of the stent jacket.

In embodiments, the assembly includes at least one extension of the compression sheath, the at least one extension being positioned between at least a portion of the stent jacket and at least a portion of the radially expandable stent.

In embodiments, the radially expandable stent comprises a metallic base from the group consisting of: stainless steel, nitinol, tantalum, MP35N alloy, a cobalt-based alloy, platinum, titanium, or other biocompatible metal alloys.

In embodiments, the radially expandable stent comprises a bio degradable/bio-absorbable base from the group consisting of: PGLA, PLLA, PLA, bio-resorbable magnesium, or other bio resorbable compounds.

In embodiments, the compression sheath includes a wall having a thickness of at least about 0.2 millimeters.

In embodiments, the compression sheath includes a wall having a thickness of more than about 0.5 millimeters.

In embodiments, the knitted jacket, the compression sheath, the stent holding apparatus, the buffering elements, the restrainer belt, and the woven belt, comprise a material selected from the group consisting of: polyethylene, polyvinyl chloride, polyurethane and nylon.

In embodiments, the knitted jacket, the compression sheath, the stent holding apparatus, the buffering elements, the restrainer belt, and the woven belt, comprise a material selected from the group consisting of nitinol, stainless steel shape memory materials, metals, synthetic biostable polymer, a natural polymer, and an inorganic material. In embodiments, the biostable polymer comprises a material from the group consisting of: a polyolefin, a polyurethane, a fluorinated polyolefin, a chlorinated polyolefin, a polyamide, an acrylate polymer, an acrylamide polymer, a vinyl polymer, a polyacetal, a polycarbonate, a polyether, a polyester, an aromatic polyester, a polysulfone, and a silicone rubber.

In embodiments, the natural polymer comprises a material from the group consisting of: a polyolefin, a polyurethane, a Mylar, a silicone, and a fluorinated polyolefin.

In embodiments, the knitted jacket, the compression sheath, the stent holding apparatus, the buffering elements, the restrainer belt, and the woven belt, comprise a material having a property selected from the group consisting of: compliant, flexible, plastic, and rigid.

In embodiments, the balloon comprises a biologically compatible elastomeric material, or semi-compliant material, for example: rubber, silicon rubber, latex rubber, polyethylene, polyethylene terephthalate, Mylar, and/or polyvinyl chloride.

In embodiments, the balloon has an inflation diameter of between 1.5 and 6.0 millimeters, depending on the cross sectional diameter of the lumen. In larger vessels, the balloon and the filter optionally are manufactured to have larger maximal diameters. In smaller vessels, for example to reduce the bulk of the contracted stent and filter, smaller maximal diameters, hence less reduced material in stent and filter, may be contemplated.

According to yet a further aspect of the invention, there is provided an assembly for opening a vessel lumen comprising: a radially expandable stent configured to open a vessel lumen, the radially expandable stent comprising a curved wall having a proximal portion, a distal portion and a lumen connecting the proximal portion and the distal portion, a jacket comprising a tubular wall that substantially surrounds an exterior surface of the radially expandable stent, and at least one retainer belt comprising at least two portions: at least one first portion that slidingly passes through at least one portion of the tubular wall of the jacket; and at least one second portion comprising at least one folded retainer belt portion that extends into the lumen of the radially expandable stent.

In embodiments, at least a portion of the vessel is stenotic. In embodiments, the vessel comprises an artery.

In embodiments, the at least one retainer belt includes at least one circumferential portion that passes circumferentially around the radially expandable stent. In embodiments, the at least one folded retainer belt portion is operatively associated with an inner wall of the radially expandable stent when the radially expandable stent is in a contracted configuration.

In embodiments, the stent comprises a self-expanding stent. In embodiments, the assembly includes a catheter portion aligned with the lumen of the self expanding stent such that one folded retainer belt portion is pressed between the curved wall of the self expanding stent and the catheter portion.

In embodiments, the assembly is configured such that as the jacket expands, a portion of the at least one folded retainer belt portion is pulled free of the operative association with the inner portion of the curved wall. In embodiments, following expansion of the jacket, the at least one folded retainer belt portion circumferentially encircles at least a portion of the self expanding stent. In embodiments, the assembly includes a balloon catheter having an inflatable tip substantially aligned with the lumen of the radially expandable stent such that upon inflation the balloon tip causes the radially expandable stent to expand radially outward.

In embodiments, the assembly is configured such that when the radially expandable stent is in a contracted configuration, the balloon is configured to press the at least one folded retainer belt portion against an inner portion of the curved wall of the radially expandable stent.

In embodiments, the assembly is configured such that as the jacket expands, a portion of the at least one folded retainer belt portion is pulled free of the operative association with the inner portion of the curved wall.

In embodiments, following expansion of the jacket, the at least one folded retainer belt portion circumferentially encircles at least a portion of the radially expandable stent.

In embodiments, the jacket of the stent comprises a material manufactured by a process from the group consisting of: interlacing knitting, interlocked knitting, braiding, interlacing, and/or dipping a porous mold into one or more reagents. In embodiments, the jacket of the stent comprises an elastomeric material. In embodiments, the elastomeric material comprises a rubber.

According to still a further aspect of the invention, there is provided an assembly for opening a stenotic lumen, the assembly comprising: a radially expandable stent configured to open a stenotic lumen, the radially expandable stent comprising a curved wall having an exterior surface, and a jacket comprising a curved wall having an interior surface, the interior surface moveably juxtaposed against the stent exterior surface.

In embodiments, the assembly includes at least one connector that connects a portion of the jacket to the stent. In embodiments, the connection between the jacket and the filter occurs in the proximal portions of the jacket and the filter. In embodiments, the connection between the jacket and the filter occurs in the distal portions of the jacket and the filter.

In embodiments, the assembly includes a fold in the jacket that folds onto an internal surface of the stent. In embodiments, the fold in the jacket is operatively associated with a proximal end of the stent. In embodiments, the fold in the jacket is operatively associated with a distal end of the stent.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1-8 show deployment of balloon expandable stents and knitted jacket assemblies, according to embodiments of the invention;

FIGS. 9-19 show deployment of radially expandable stents and knitted jacket assemblies, according to embodiments of the invention.

DESCRIPTION OF THE PREFERRED EMBODIMENTS

Figure 1:
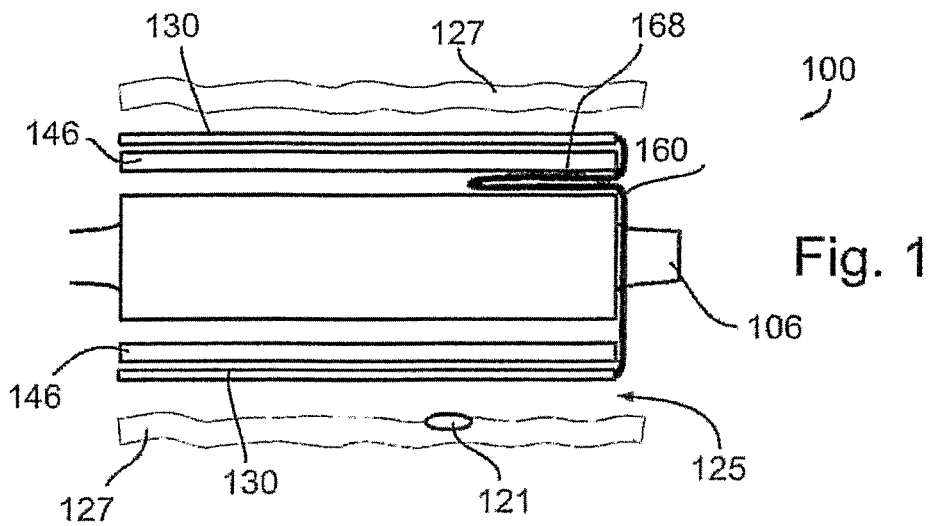

The present invention relates to stent jackets externally on the stent and protected from damage during stent deployment.

The principles and uses of the teachings of the present invention may be better understood with reference to the accompanying description, Figures and examples. In the Figures, like reference numerals refer to like parts throughout.

Before explaining at least one embodiment of the invention in detail, it is to be understood that the invention is not limited in its application to the details set forth herein. The invention can be implemented with other embodiments, and can be practiced or carried out in various ways.

It is also understood that the phraseology and terminology employed herein is for descriptive purpose and should not be regarded as limiting.

Unless otherwise defined, all technical and scientific terms used herein have the same meaning as commonly understood by one of ordinary skill in the art to which the invention belongs. In addition, the descriptions, materials, methods, and examples are illustrative only and not intended to be limiting. Methods and materials similar or equivalent to those described herein can be used in the practice or testing of the present invention.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

As used herein, "a" or "an" mean "at least one" or "one or more". The use of the phrase "one or more" herein does not alter this intended meaning of "a" or "an".

FIG. 1 shows a schematic view of an assembly 100 for opening a vessel 127, comprising a balloon expandable stent 146 surrounded by a jacket 130. The location of jacket 130 externally on stent 146 protects the tissue of vessel 127 during expansion of stent 146.

Additionally, the location of jacket 130 externally on stent 146 provides substantial protection against potential debris 121 from entering a vessel lumen 125 during expansion of stent 146.

Figures 2, 3:
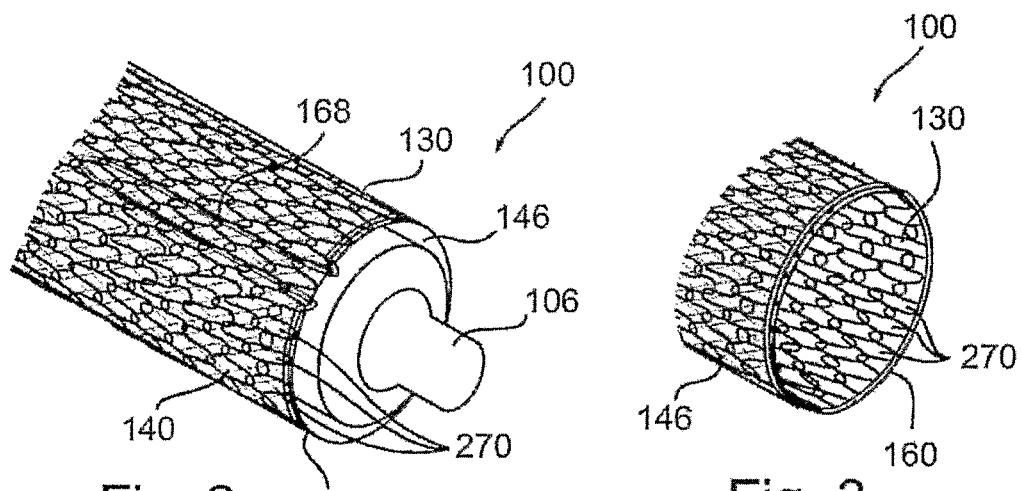

FIG. 2 shows detail of jacket 130, which is formed into a tubular structure comprising a plurality of interconnected loops 270.

Assembly 100 includes a catheter balloon 106 that causes expandable stent 146 to expand when balloon 106 expands, thereby expanding jacket 130.

Assembly 100 further comprises a retainer belt 160 that passes circumferentially through loops 270, thereby preventing runs from forming in jacket 130 during positioning and/or expansion of stent 146.

In embodiments, retainer belt 160 exits loops 270 to form a folded retainer belt portion 168. As can best be seen in FIG. 1, with balloon 106 in an unexpanded configuration, folded retainer belt portion 168 is wedged, herein positioned, between balloon 106 and stent 146, thereby maintaining jacket 130 slidingly in place around stent 146 without additional securing means.

Expandable jacket 130 optionally has a different coefficient of expansion from stent 146, however due to the sliding attachment, stent 146 expands at a different rate without affecting the expansion of expandable jacket 130. In this manner expandable jacket 130 is easily held snugly on the external surface of stent 146, thereby being positioned to, in some embodiments, efficiently prevent stenotic debris 121 from entering into a vessel lumen 125.

Alternative configurations for stent 146 slidingly attached to stent jacket 130 will be discussed below with respect to FIGS. 20a-20f.

While having a single folded belt 168, in some embodiments, greater expansion may be desirable, necessitating a plurality of folded retainer belts 168.

Figure 4A:
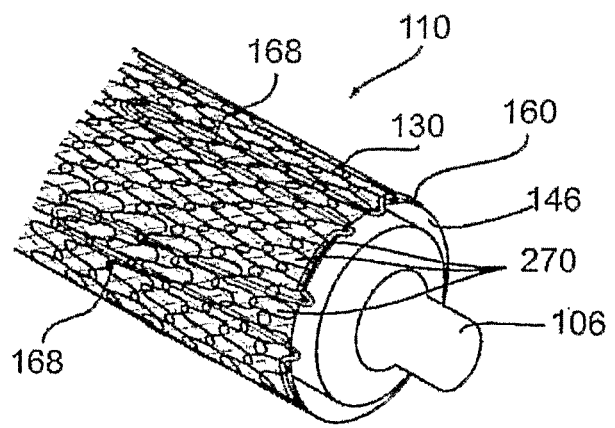

FIG. 4a shows an assembly 110 comprising two folded retainer belt portions 168 positioned distally between stent 146 and balloon 106 that unfold to form a substantially circumferential retainer belt 160 upon expansion of stent 146 as previously shown in FIG. 3. Two folded distal retainer belt portions 168 optionally provide greater stability to jacket 130 on stent 146 and/or allow the length of each folded retainer portion 168 to have a shorter length while allowing full outward radial expansion of jacket 130.

In some embodiments, alternative placement of two folded retainer belts portions 168 may be desirable, for example when controlled expansion of stent jacket 130 is required at both ends of stent 146.

Figure 4B:
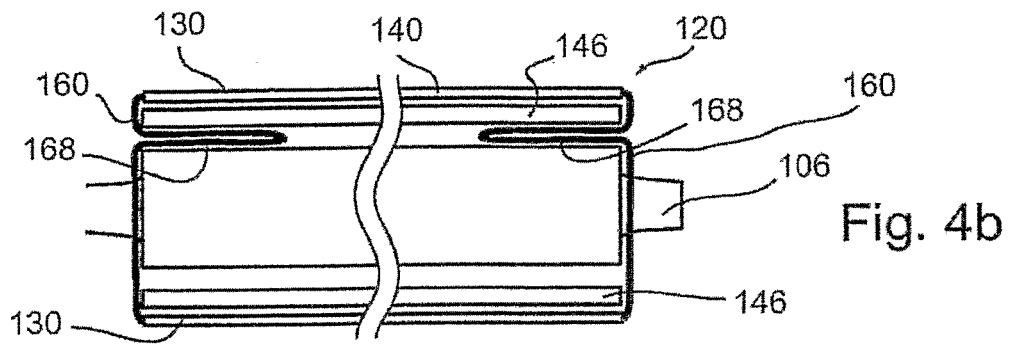

FIG. 4b shows an assembly 120 comprising dual retainer belts 160 located along proximal and distal loops 270, thereby preventing runs from forming at either end portion of jacket 130 during positioning and/or expansion of stent 146.

In embodiments, one or more retainer belts 160 are optionally secured around jacket 130 substantially in the middle of jacket 130 to provide additional protection against runs caused, for example, by tears in jacket 130. The many possible positions and configurations of retainer belt 160 are well known to those familiar with the art.

In embodiments, ensuring smooth movement during unfolding of retainer belt 168 is desirable.

Figure 4C:
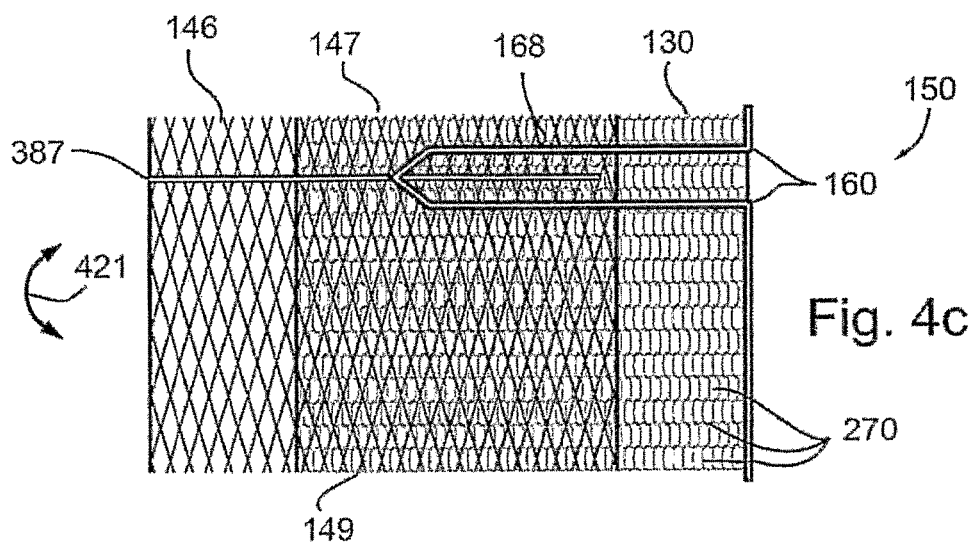

FIG. 4c shows a plan view of a stent assembly 150 embodiment including self-expanding stent 146, with stent jacket 130 below stent 146. For clarity, stent jacket 130 is shown a bit distal to stent 146. Folded retainer belt portion 168 is above stent 146, along a support rail 387. Support rail 387 allows smooth movement of folded belt retainer 168 during expansion of stent 146 without getting caught against the diamond-shaped struts of stent 146.

To form stent 146 and jacket 130 into tubular assembly 150, edges 147 and 149 are brought together in directions 421.

While stent jacket 130 has been shown on balloon expandable stents, stent jacket 130 can optionally be configured for use with other types of stents while allowing the sliding attachment arrangement between stent jacket 130 and stent 146.

Figure 4D:
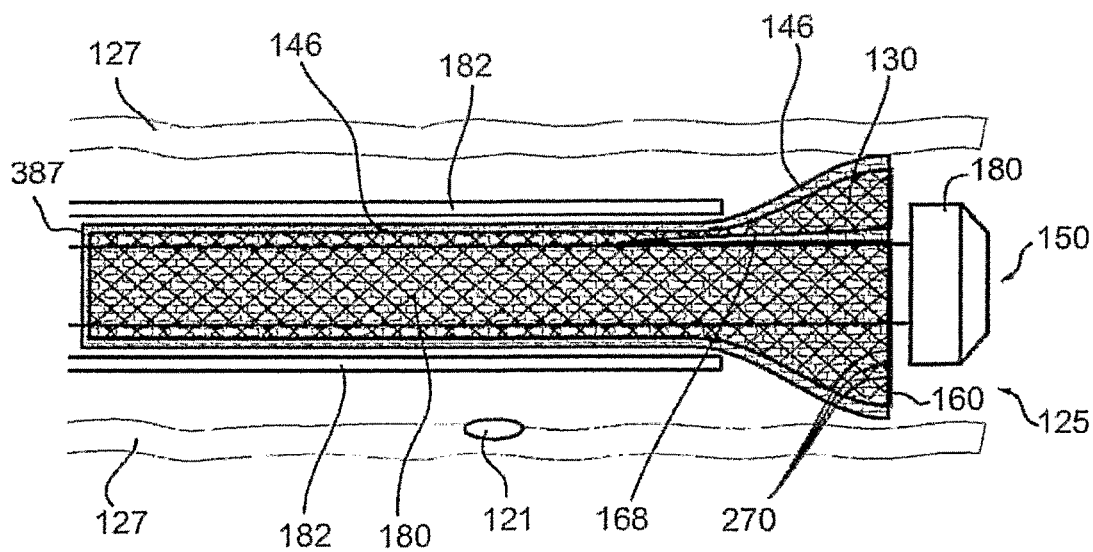

In FIG. 4d, tubular stent assembly 150 is shown in position around a spindle holder 180, emerging from a compression sheath 182, with stent 146 and jacket 130 in substantial tubular alignment. Folded retainer belt portion 168 is positioned against an internal surface of stent 146 and held in position by the pressure of spindle holder 180;

ensuring that stent jacket 130 assembly remains on stent 146 even though stent jacket 130 is slidingly located on an external surface of stent 146.

Figure 4E:
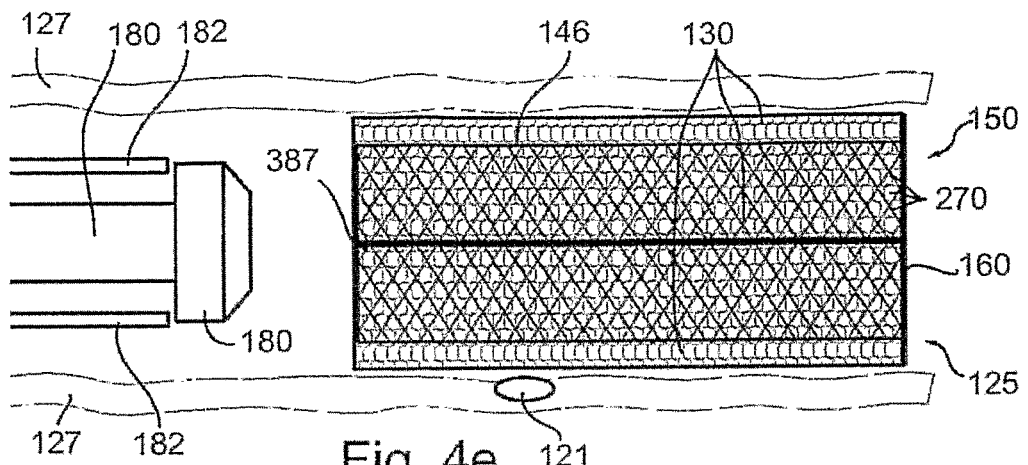

As in assembly 110, during expansion, folded retainer belt 168 is drawn distally through forward loops 270 of jacket 130 so that, as seen in FIG. 4e, assembly 150 fully expands in vessel lumen 125 and jacket 130 presses against vessel walls 127.

While belt 160 is shown passing through loops 270 of jacket 146 which is knit, in embodiments, jacket 130 comprises a woven fabric, rather than a knit fabric, and folded retainer belt portion 168 is woven through a first portion and a second portion of jacket 130 with folded retainer belt portion 168 positioned between the first and second portions of the woven fabric.

In other embodiments jacket 130 comprises a porous sheet comprising, for example rubber material, and belt 160 is looped through a first portion and a second portion of jacket 130 with folded belt portion 168 positioned between the first and second loop portions through jacket 130 and against an internal surface of stent 146. The many types of materials that are suitable for jacket 130 and the many configurations of folded belt portion 168 therethrough, are well known to those familiar with the art.

In the above noted embodiments of assemblies 100, 110, 120 and 125, the positioning of folded retainer belt portion 168 allows jacket 130 to slidingly move on stent 146 without adhesives, weaving or sewing to secure the fabric of jacket 130 against the external surface of stent 146. In this manner, externally located stent jacket 130 expands independently of, and easily slides with respect to, stent 146 during expansion. In this manner stent 146 and jacket 130, as noted above, can function efficiently in spite of having different coefficients of expansion.

Additionally, in being positioned externally to stent 146 in embodiments, jacket 130 prevents stenotic debris 121 from entering vessel lumen 125 during expansion.

As used herein, any reference to a "knitted material" includes any material that is manufactured by a knitting process, including, inter alia: a material knitted from a single fiber, similar to the process used in pantyhose nylon; a double fiber knit, referred to as a "double knit material"; and any material subject to runs whether from the above-noted "flipping" and/or from tears, for example in the body of the material.

Additionally, as used herein, any reference to a "knitted material" includes materials knitted from fibers, either monofilament or multifilament fiber of, inter alia, polyethylene, polyvinyl chloride, polyurethane and nylon stainless steel nitinol, or any other metal.

In embodiments, folded retainer belt 168 may require greater length to fully encircle stent 146 upon expansion.

Figure 5:
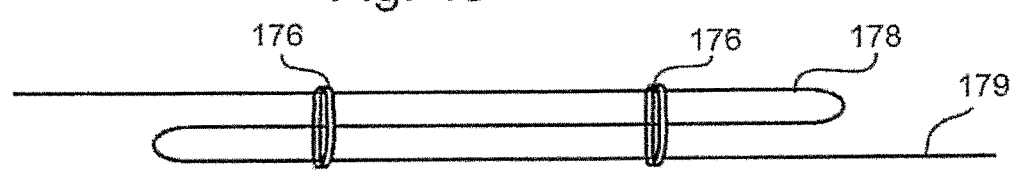

FIG. 5 shows a retainer belt 179 that is folded into multiple folds 178. Multiple folds 178 are maintained in the folded configuration with first and second ring restrictors 176. While ring restrictors 176 are depicted, alternative embodiments for maintaining folds 178 include adhesives, clips, staples, and/or stitches. Alternatively, a single restrictor 176 is optionally used to removably secure multiple folds 178.

Figure 6:
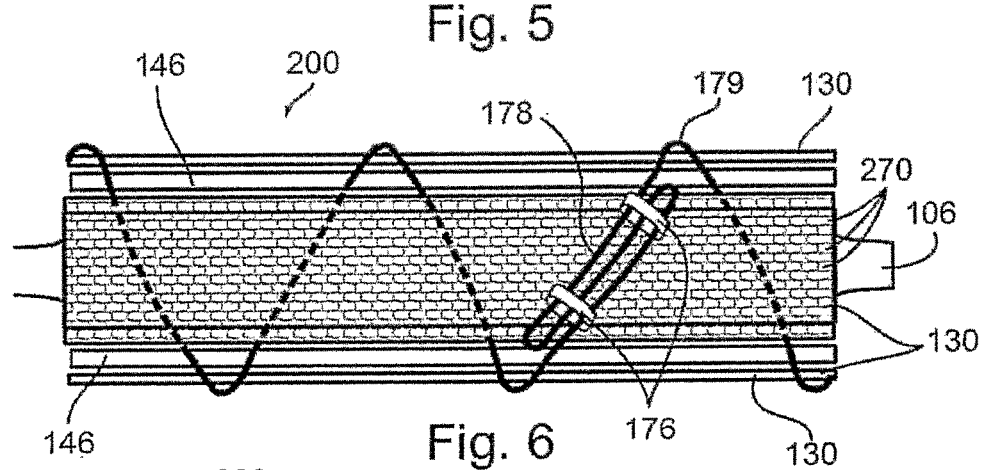

As seen in FIG. 6, a first end portion of retainer belt 179 is attached to a distal portion of jacket 130, and a second end portion of retainer belt 179 is attached to a proximal portion of jacket 130. Portions of retainer belt 179 extending from either end portions of multiple folds 178 are woven through loops 270, thereby protecting jacket 130 from developing runs during deployment.

Figure 7:
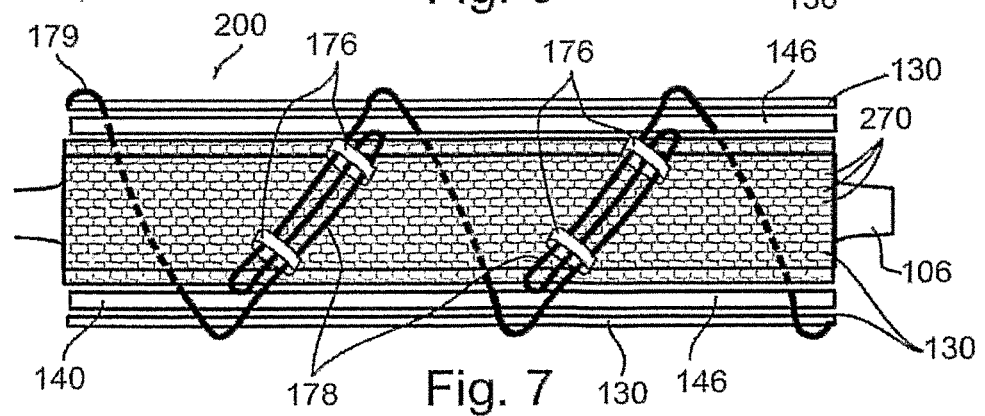

FIG. 7 shows multiple folds 178 that are held in folded configuration by two pairs of restrictor rings 176 on each fold 178.

As seen in FIG. 8, stent 146 and jacket 130 have been radially expanded, so that retainer belt portions that had multiple folds 178 have been pulled substantially free of restrictor rings 176, and retainer belt 179 forms a substantially monotonous helix around expanded jacket 130.

While retainer belt 179 is shown in a helical configuration when stent 146 is both in the expanded and contracted (FIG. 5) configurations, retainer belt 179 optionally circumferentially surrounds jacket 130 radially, in a plane that is perpendicular to the longitudinal axis of stent 146.

Alternatively, a first retainer belt 179 is formed into a clockwise helix around jacket 130 and a second retainer belt 179 is formed into a counterclockwise helix around jacket 130, thereby forming, for example, one or more "x" patterns on jacket 130.

Additionally, at least a portion of retainer belt 179 optionally comprises an elastomeric material that allows expansion of retainer belt 179 beyond the length of the material contained within folded portions 178. The many configurations and materials for retainer belt 179 are well known to those familiar with the art.

Whether jacket 130 is knitted or whether jacket 130 is manufactured by a variety of other techniques, jackets 130 in conjunction with stents 146 that are self-expanding are subject to damage during deployment. For example as seen in FIG. 9, a self-expanding stent assembly 200 is contained inside vessel lumen 127. Self-expanding stent assembly 200 comprises a self-expanding stent 240 and a jacket 132 that are compressed against a spindle holder 180 by a compression sheath 182. During expansion, jacket 132 may be damaged by compression sheath 182 due, for example, to friction and/or catching fibers on sheath 182.

Figure 11A:
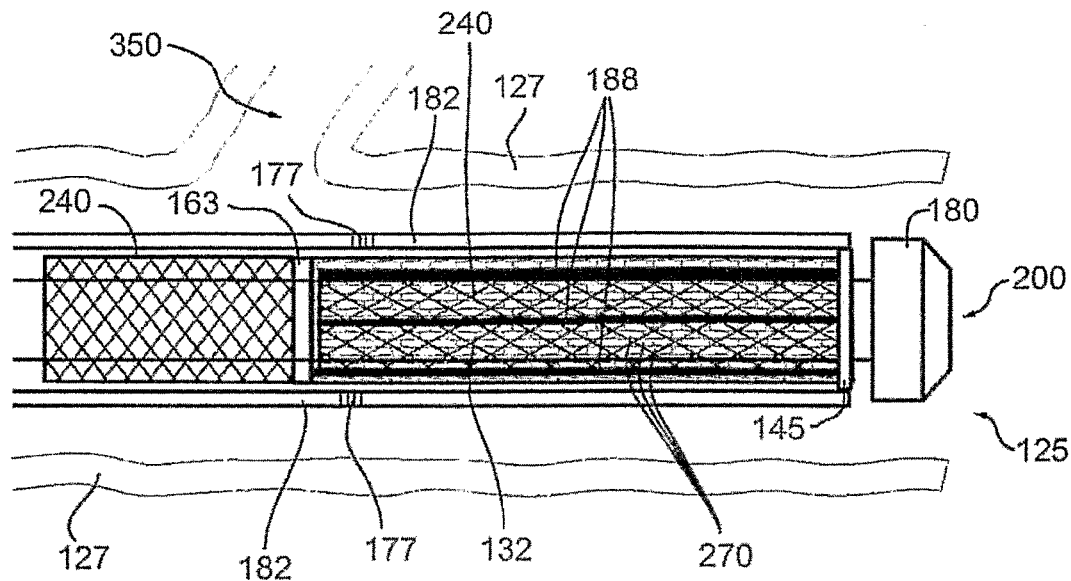

As seen in a cross sectional view in FIG. 10 and a side view in FIG. 11A, to prevent damage by sheath 182, buffering elements 188 are interposed between jacket 132 and compression sheath 182.

Figure 11B:
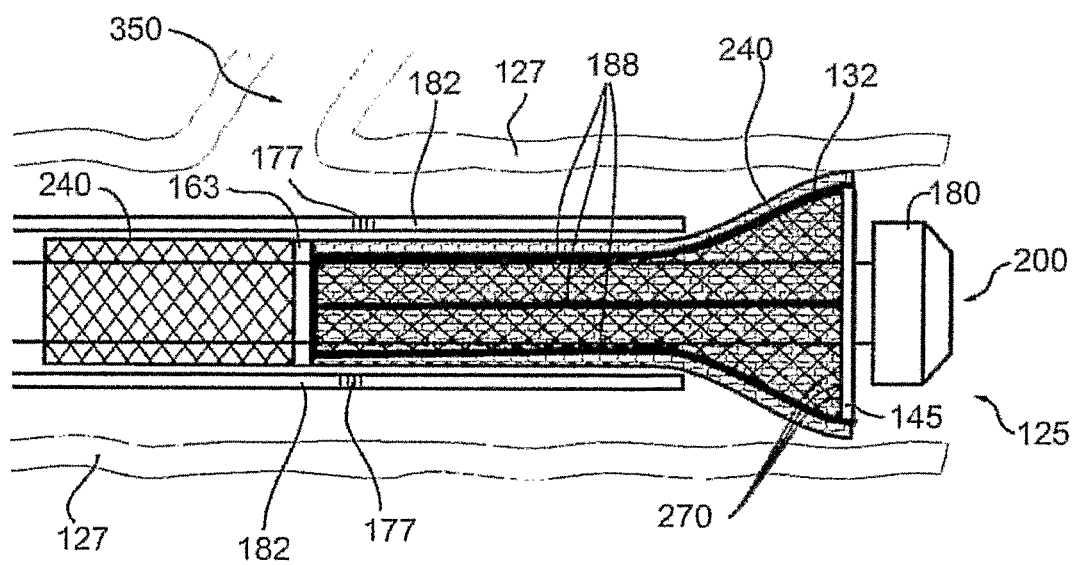

As seen in FIG. 11B, buffering elements 188 prevent damage to jacket 132 during removal of compression sheath 182 and expansion of stent 240.

Figure 12:
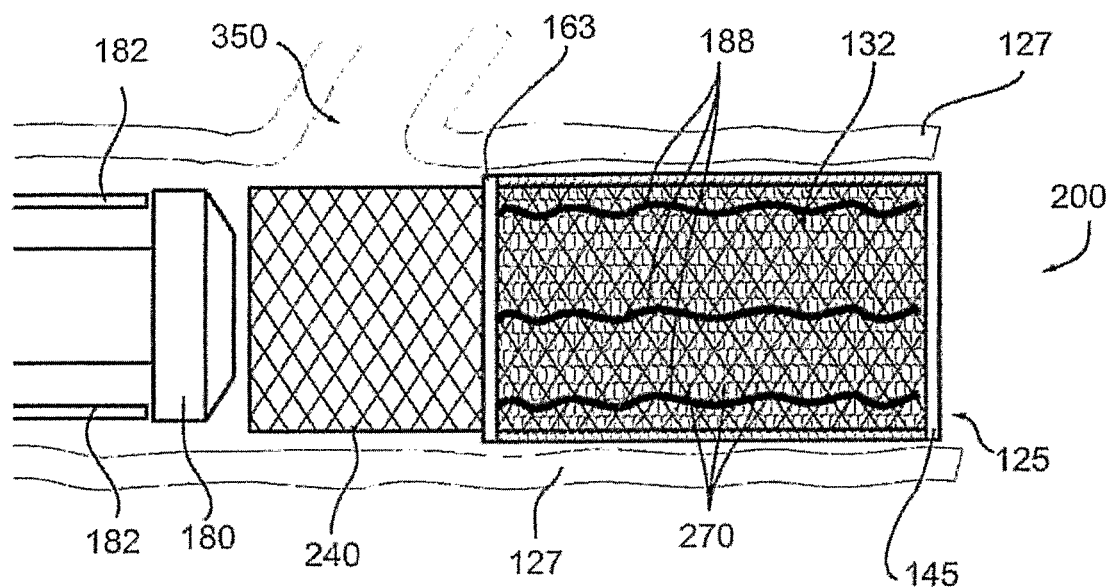

The longitudinal configuration of buffering elements 188 can be appreciated from FIG. 12, in which stent 240 is fully expanded within vessel lumen 127. There are many additional configurations possible for buffering elements 188, for example a helical configuration, not shown.

Additionally, there are many methods for securing buffering elements 188 to jacket 132. For example, as shown, buffering elements 188 comprise cords attached to the outer surface of jacket 132. Optionally, buffering elements 188 are attached at the distal and proximal portions of jacket 132 or stent 240.

As used herein, the terms proximal and proximally refer to a position and a movement, respectively in an upstream direction in vessel lumen 127. By way of example, compression sheath 182 is proximal to stent 240. As used herein, the terms distal and distally refer to a position and a movement, respectively, in a downstream direction in vessel lumen 127. By way of example, stent 240 is distal to compression sheath 182.

As noted above, stent 240 and jacket 132 typically have different coefficients of expansion but are protected by the sliding attachment noted above. However, with respect to compression sheath 182, jacket 132 is held in compression and slidingly moves out of compression sheath 182. During expansion, the different coefficients of expansion in conjunction with the radial inward pressure by sheath 182 may still have the potential to create damage during radial expansion of stent 240.

Figure 13:
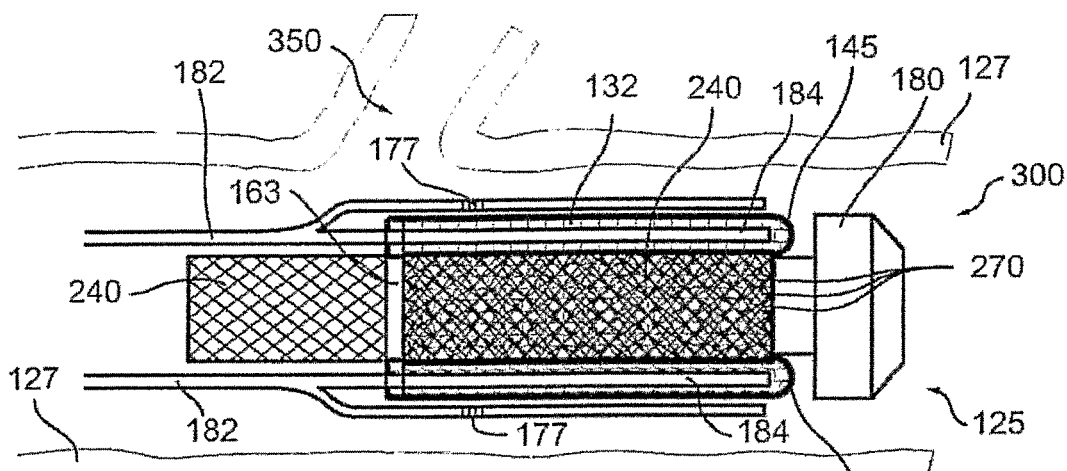

FIG. 13 shows an assembly 300 in which a buffering element tube 184 is interposed between an internal surface of jacket 132 and an external surface of stent 240 to prevent damage of jacket 132 during expansion.

Figure 14:
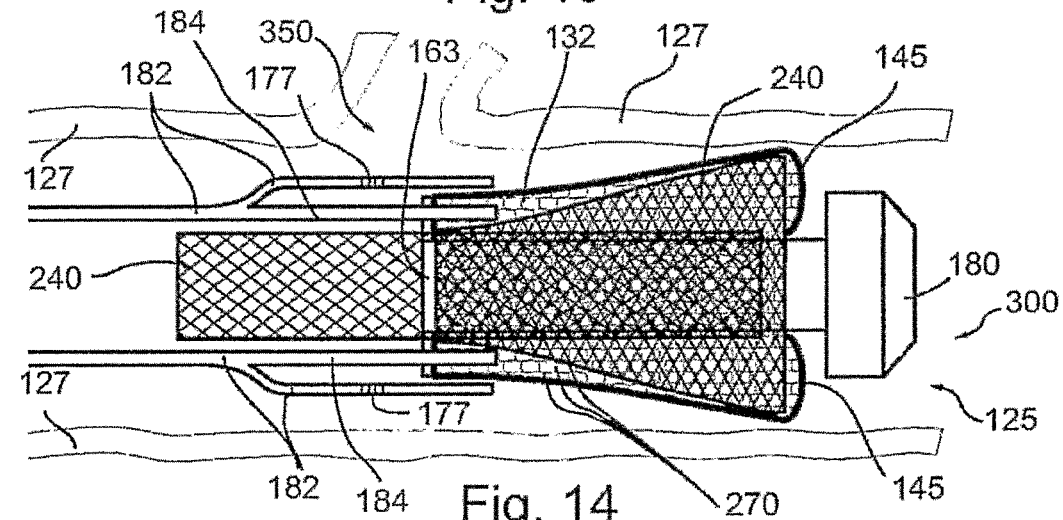
Figure 15:
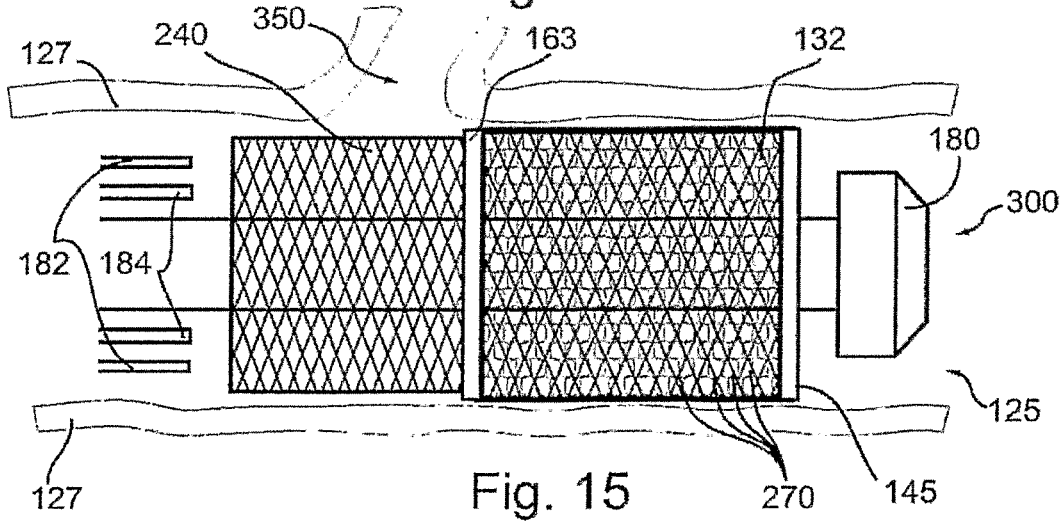

In FIG. 14, stent 240 is shown emerging from buffering element tube 184 while jacket 132 is shown emerging from between compression sheath 182 and buffering element tube 184. In this manner, as seen in FIG. 15, stent 240 and jacket 132 are successfully expanded within vessel lumen 127 without damage to jacket 132 despite the above-noted difference in coefficient of expansion.

Proper positioning of stent 240 is important so that stent 240 does not block, for example, a branch vessel 350. To determine positioning of stent 240 markers may be placed on stent 240 and/or jacket 132. However, this is not always accurate enough.

For example, if stent jacket 132 protrudes beyond the proximal and/or distal boundaries of stent 240, a radiopaque marker on stent 140 does not provide the surgeon with information as to the position of the extent of stent jacket 132. It is therefore appropriate to place markers, for example, on positioning equipment.

As seen in FIGS. 11, 12, 13, 14 and 15, sheath 182 optionally incorporates a radiopaque marker 177 distally. Radiopaque marker 177 is optionally offset proximal to the distal portion of sheath 182, for example to demonstrate to the surgeon the future location of the distal end of jacket 132 following radial expansion of stent 240.

Alternatively, stent jacket 132 includes a proximal radiopaque marker 163. Distal markers 145 and/or proximal markers 163 apprise the surgeon of the distal-most and/or proximal-most boundaries, respectively, of stent jacket 132 thereby providing the surgeon with precise orientation information.

In embodiments, markers 146 and 163 are placed on multiple locations to provide further information to the surgeon.

For example, radiopaque markers 146 and 163 can be configured to incorporate two markers each. A first marker 146, demonstrates the edge of stent jacket 132, signifying where stent 240 will be following expansion. A second marker 163, provides position information on the boundaries of stent 240 either before, during or after expansion of stent 240.

In this way, the surgeon is not only apprised of the position of jacket 132, but also the position of the underlying support to jacket 132, provided by stent 240, and thereby avoids blocking branch vessel 350.

Radiopaque markers 163, 145 and 177 optionally comprise gold or other radiopaque marking material.

Thus far, the invention has been focused on preventing damage to stent jackets comprising knitted material and damage to jackets 132 on a self expanding stent comprising any material.

With respect to knitted jackets 140, if runs 198 (FIG. 17) could be controlled in a manner that substantially prevent fibers from entering the lumen of stent 240, runs 198 could optionally aid in radial expansion and bulk reduction of jacket 130.

Figure 16:
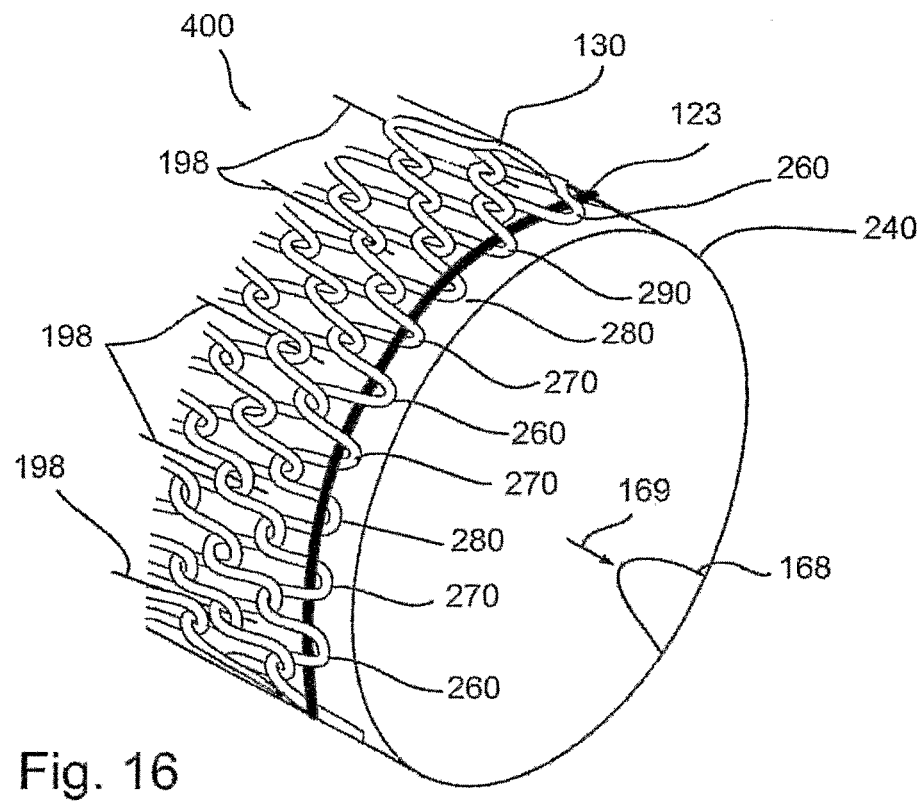

FIG. 16 shows a stent assembly 400 comprising contracted self-expanding stent 240 surrounded by controlled run knitted jacket 130 in which a retainer belt 123 passes behind a loop 260, through a second loop 270 and in front of a third loop 280.

Figure 17:
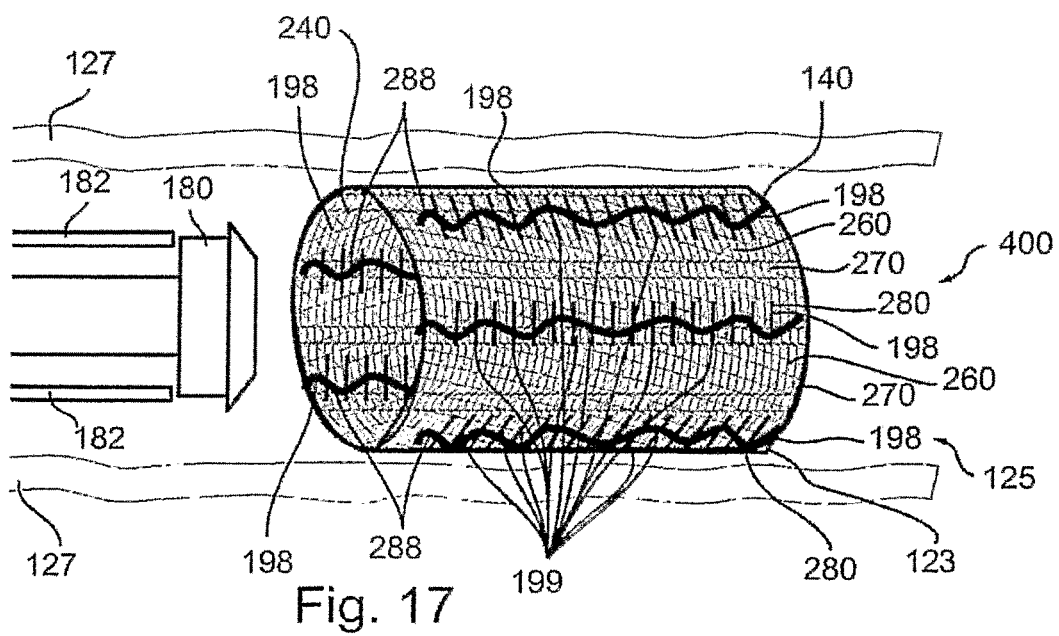

Upon expansion of stent 240, as seen in FIG. 17, rows of loops extending from loops 270 are protected from forming runs 198 by retainer belt 123. In distinct contrast rows of loops extending from loops 260 and 280 are not protected and form runs 198.

To prevent run fibers 199 from entering the lumen of stent 240, run support cords 288 are located between stent 240 and controlled run jacket 140 along rows of loops extending from loops 260 and 280. In embodiments, run supports 288 are longitudinally placed between stent 240 and jacket 130.

As noted above, runs 198 aid in providing significant radial expansion of stent jacket 140. Without runs 198, expansion of jacket 140 is limited solely by the radial stretch of loops 270. Runs 198, however, result in lengthened transverse run fibers 199, thereby providing a mode for achieving radial expansion in addition to the stretch of loops 270.

Runs 198 potentially reduce the amount of material required to achieve a given radial expansion as compared to jackets 140 fully protected with retainer belt 123. Thus, controlled run jacket 140 has the potential to substantially reduce bulk so that contracted assembly 400 more easily maneuvers through vessel lumen 127.

Attachment of run supports 288 may be configured in any one of several manners. In embodiments, run supports 288 include a proximal portion attached to a proximal portion of stent 240 and/or jacket 130, and a distal portion attached to a distal portion of stent 240 and/or jacket 130. In embodiments, run supports 288 include a central portion attached to a central portion of stent 240 and/or jacket 130.

In addition to fostering controlled runs that reduce bulk, retainer belt 168 may be configured to have increased expansion, as noted above. For example, in embodiments, retainer belt 123 includes folded retainer belt portion 168 (FIG. 16). During expansion of self-expanding stent 240, folded retainer belt portion 168 moves in a direction 169 and unfolds to become circumferentially contiguous with retainer belt 123.

In embodiments that include folded retainer belt portion 168, retainer belt 123 optionally comprises relatively stiff materials and folded retainer belt portion 168 substantially provides necessary expansion of retainer belt 123.

In other embodiments, retainer belt 123 comprises moderately stretchable materials that aid retainer belt 123 in expanding in conjunction along with folded retainer belt portion 168.

In further embodiments in which folded retainer belt portion 168 is not present, retainer belt 123 optionally comprises elastomeric materials that provide all necessary expansion of retainer belt 123 during expansion of self-expanding stent 240. The many options for material properties and configurations of retainer belt 123 are well known to those familiar with the art.

The location and configuration of supports for runs 199 are not restricted to run support cords 288 located between controlled run jacket 140 and stent 240. As seen in a plan view of assembly 400 (FIG. 18), run support rails 388 may be integrated into stent 240.

As seen in FIG. 19, run supports 388 substantially align with runs 198 to prevent the above-noted run fibers from entering the lumen of stent 240.

As is the case with run support cords 288, run support rails 388 prevent run fibers 199 from entering the lumen of implanted stent 240. In distinct contrast, run fibers 288 unsupported by support rails 388, may generate dangerous blood turbulence and/or thrombus formation, noted above.

In embodiments, stent 240 comprises a bio degradable material from the group of materials consisting of: PGLA, PLLA, PLA, bio-resorbable magnesium, or other biodegradable materials.

As used herein, the term biodegradable base refers to any material that degrades and/or is absorbed by an in vivo environment over a period of time. Further, as used herein, the term biodegradable is interchangeable with the terms bio-absorbable and bio-resorbable.

In embodiments, stent 240 typically includes a metallic base, for example stainless steel, nitinol, tantalum, MP35N alloy, a cobalt-based alloy, platinum, titanium, or other biocompatible metal alloys.

In embodiments, stent 240 comprises an alloy that includes tantalum, tungsten, and zirconium: tantalum from about 20% to about 40% by weight; tungsten from about 0.5% to about 9% by weight; and zirconium from about 0.5% to about 10% by weight.

In alternative embodiments, self-expanding stent 240 comprises an alloy such as nitinol (Nickel-Titanium alloy), having shape memory characteristics.

Shape memory alloys have super-elastic characteristics that allow stent 240 to be deformed and restrained on spindle 180 during insertion through vessel lumen 127. When compression sheath 182 is removed (FIG. 11) and self-expanding stent 240 is exposed to the correct temperature conditions, the shape memory material returns to an original expanded configuration. Self-expanding stent 240, for example, is superelastic in the range from at least about twenty-one degrees Centigrade to no more than about thirty-seven degrees Centigrade.

As used herein, a nitinol alloy refers to an alloy comprising between about at least 50.5 atomic percent Nickel to no more than about 60 atomic percent Nickel with the remainder of the alloy being Titanium. The term nitinol is intended to refer to a two-component memory metal stent discussed above as well as any other type of known memory metal stent.

In embodiments, jacket 130 contains apertures 270 (FIG. 16) having diameters of between at least about 20 microns and no more than about 200 microns. In embodiments, substantially all apertures 270 have substantially similar diameters. In other embodiments, apertures 270 have variable diameters.

In embodiments, jacket 130 has a thickness of between at least about 20 microns and no more that about 200 microns.

In embodiments, unexpanded stent 240 has a diameter of at least about 0.3 millimeters and no more than about 3.0 millimeters; while expanded stent 240 has a diameter of at least about 1.0 millimeter to not more than about 8.0 millimeters.

In embodiments, jacket 130 and/or stent 240 comprise materials that are coated and/or imbued with one or more active pharmaceutical agents for the purpose of preventing infection, inflammation, coagulation and/or thrombus formation.

In embodiments, jackets 140 that are moveably attached to stent 240 may be manufactured by any process including knitting, braiding, knotting, wrapping, interlacing, electro-spinning, and/or dipping a porous mold into one or more reagents.

FIGS. 20a-20f show stents having moveably attached jackets, according to embodiments of the invention using a moveable connection that allows many types of jacket materials to be deployed with stent 140.

Figure 20A:
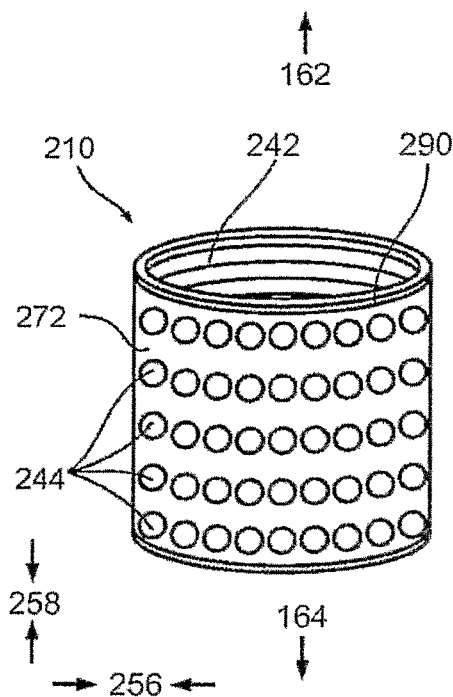
FIGS. 20a-20f show stents having moveably attached jackets, according to embodiments of the invention.
Figure 20B:
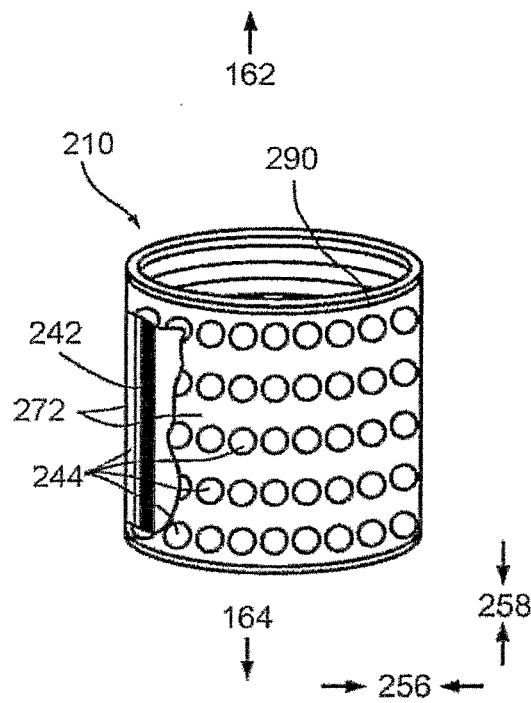

FIG. 20a shows a jacketed stent 210 comprising an outer jacket 272 and an inner stent 242 that are connected by distal connection 290. As seen in FIG. 20b, besides distal connection 290, stent 242 and jacket 272 are substantially free of further connection.

During radially outward expansion in a direction 256, stent 242 typically contracts considerably in directions 258 while jacket 272 remains relatively stationary with respect to stent 242. Jacket 272 allows contraction of stent 242 while buffering shear forces generated by stent 242 on lesion 144, thereby substantially preventing generation of unwanted and dangerous debris 130 during radial expansion.

In embodiments, distal connection 290 optionally comprises a process of sewing, adhesion, gluing, suturing, riveting and/or welding. Optionally, distal connection 290 is offset proximally 164 along stent 242, for example up to and including the center of stent 242 or along distal portion of stent 242.

Figure 20C:
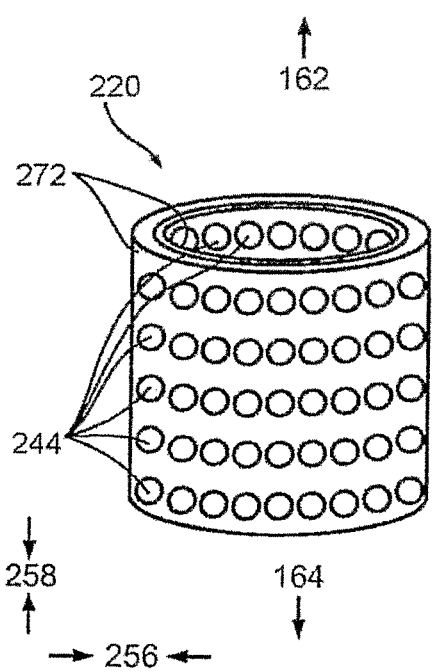
Figure 20D:
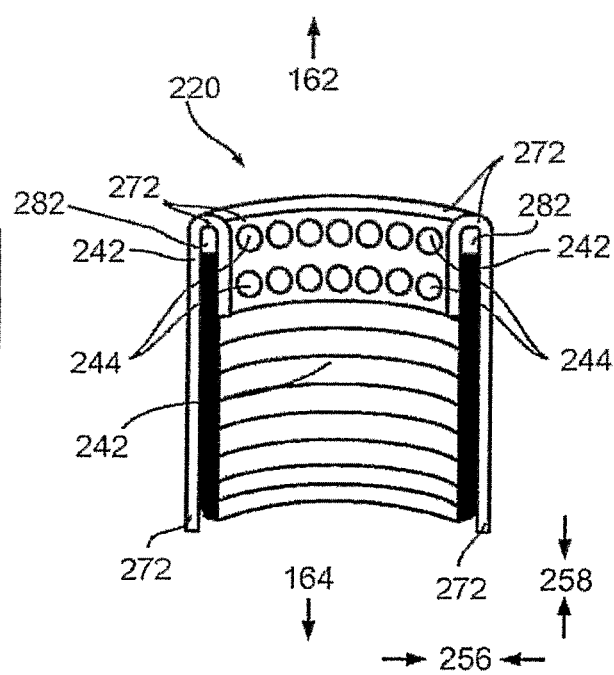

FIGS. 20c and 20d show a jacketed stent 300 in which distal portion 162 of jacket 272 is folded over distal portion 162 of stent 242. Stent 242 is therefore substantially completely unattached to jacket 272. During radially outward expansion in direction 256, contraction of stent 242 in directions 258 results in gaps 282 between stent 242 and stent jacket 272 so that the walls of vessel 127 (FIG. 1) are buffered from shear forces generated by stent contraction in directions 258.

Figure 20E:
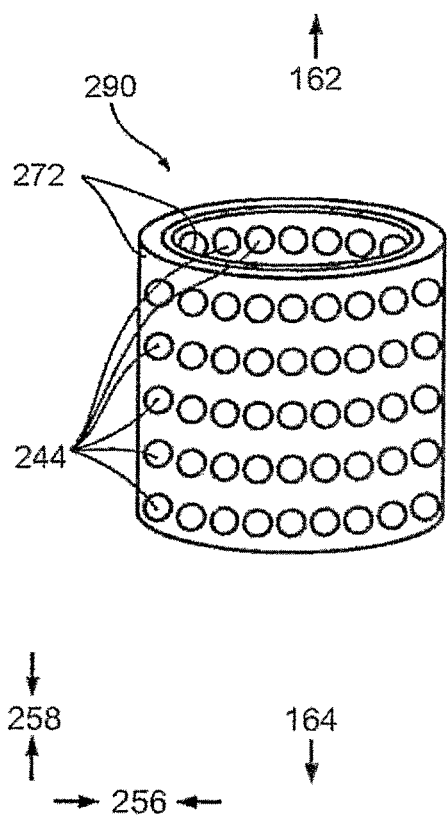
Figure 20F:
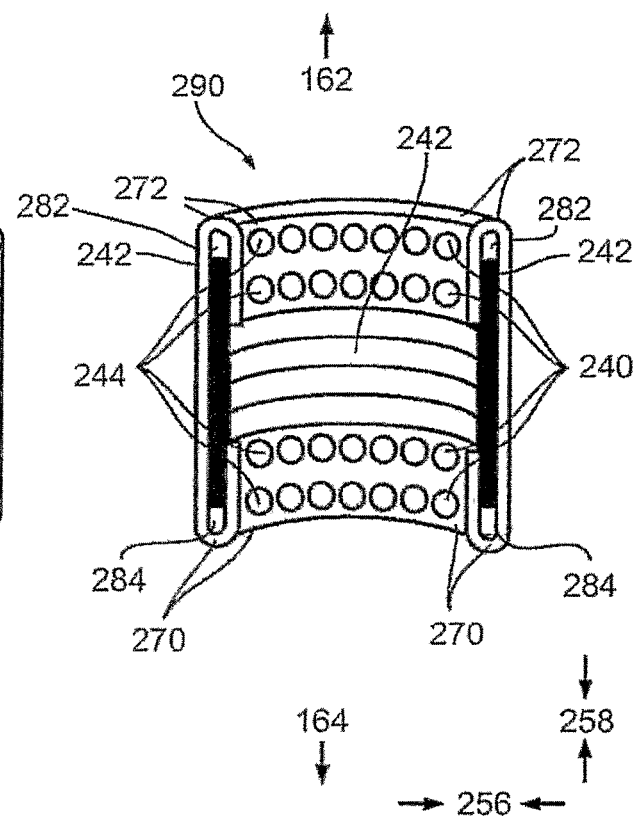

FIGS. 20e and 20f show still another embodiment in which a jacketed stent 390 comprises jacket 272 that is folded over both the proximal 162 and distal 164 aspects of stent 242. Upon expansion of stent 242, distal gap 282 and/or a proximal gap 284 optionally form due to jacket 272 remaining substantially stationary with respect to contraction in directions 258 of stent 242.

In embodiments, jacket 272 includes apertures 244 having a diameter of between at least about 3 microns and no more that about 100 microns.

In embodiments, jacket 272 contains apertures 244 that substantially prevent generated stenotic debris 121 (FIG. 1) from entering apertures 244, thereby substantially preventing the above-noted tendency for plaque to be ripped from vessel luminal aspect 140. In embodiments, apertures have diameters of between at least about 20 microns and no more than about 210 microns. In embodiments, all apertures 244 have substantially similar diameters. In other embodiments, apertures 244 have variable diameters.

The above-noted jacketed stent assemblies, including assemblies 100, 110, 120, 150, 200 210, 220, 290, 300 and 400, are optionally designed for use in a wide variety of vascular tissue including coronary, peripheral, cerebral, and/or carotid vascular tissue. Additionally the above noted jacketed stent assemblies are optionally designed for use in treating an aortic aneurysm and/or a body lumen, for example a lumen associated with pulmonary tissue.

The many materials, manufacturing methods, uses and designs of the above-noted jacketed stent assemblies are well known to those familiar with the art.

In embodiments, the knitted jacket, the compression sheath, the spindle, the buffering elements, the restrainer belt, and the woven belt, comprise materials from the group consisting of: polyethylene, polyvinyl chloride, polyurethane and nylon.

In embodiments, the knitted jacket, the compression sheath, the spindle, the buffering elements, the restraining belt, and the woven belt, comprise a material selected from the group consisting of: nitinol, stainless steel shape memory materials, metals, synthetic biostable polymer, a natural polymer, and an inorganic material. In embodiments, the biostable polymer comprises a material from the group consisting of: a polyolefin, a polyurethane, a fluorinated polyolefin, a chlorinated polyolefin, a polyamide, an acrylate polymer, an acrylamide polymer, a vinyl polymer, a polyacetal, a polycarbonate, a polyether, a polyester, an aromatic polyester, a polysulfone, and a silicone rubber.

In embodiments, the natural polymer comprises a material from the group consisting of: a polyolefin, a polyurethane, a Mylar, a silicone, and a fluorinated polyolefin.

In embodiments, the knitted jacket, the compression sheath, the spindle, the buffering elements, the restraining belt, and the woven belt, comprise materials having a property selected from the group consisting of compliant, flexible, plastic, and rigid.

It is expected that during the life of a patent maturing from this application, many relevant stent jackets and/or stent jacket materials will be developed and the scope of the term stent jacket is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity, and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Experimental Results:

The inventors have found that embodiments of the present invention of a single fiber knit stent jacket have the potential to provide possible advantages over stent jackets manufactured by the above-noted processes of braiding, knitting, wrapping, interlacing, electrospinning and/or dipping a porous mold into one or more reagents; processes often resulting in bulky jackets that make it difficult, if not impossible, to maneuver narrow stenotic vessels.

The inventors have further found that embodiments of the present invention not only provide single fiber knit thin jackets that appear to be easy to maneuver, but that prevent unraveling when cut anywhere along the materials, causing the materials to form a "run".

Runs in a stent jacket pose a serious problem as the fibers in a run protrude through the stent mesh apertures into the stent lumen, creating a potential retardation in blood flow. Even worse, fibers passing through the stent lumen can create unwanted turbulence and/or thrombus formation, thereby defeating the entire purpose of the stent.

Additionally, embodiments of the present invention have been shown to prevent flipping of the end portion loops on single fiber knit nylon, thereby further preventing runs.

In addition to the above, the inventors have found that embodiments of the present invention comprising stent jackets that moveably attach to the stent are potentially possibly easier to deploy than stent jackets deployed prior to introducing the stent (e.g. U.S. Pat. No. 6,712,842, Gifford et al, the content of which is incorporated herein in its entirety by reference), wherein the required precise alignment of the contracted stent with the expanded jacket is a difficult, hence undesirable procedure.

Further, the inventors have found that embodiments of the present invention may have advantages over external stent jackets having a similar expansion coefficient to that of the stent (e.g. U.S. Pat. No. 6,794,485, Shalaby, the content of which is incorporated herein in its entirety by reference); wherein because the external stent jacket contracts with the stent during radial expansion, the jacket fails to effectively buffer the stenotic vessel from the above-noted shear forces.

What is claimed is:

1. An assembly for opening a vessel lumen comprising:
   a radially expandable stent configured to open the vessel lumen, said radially expandable stent comprising a curved wall having a proximal portion, a distal portion, and a lumen connecting said proximal portion and said distal portion;
   a knitted stent jacket comprising a tubular wall that substantially surrounds an exterior surface of said radially expandable stent; and
   a plurality of buffering element cords having an external surface placed against an external surface of said knitted stent jacket, covering only a minor portion of a surface of the knitted stent jacket, in a manner which spaces the knitted stent jacket from an adjacent element of the assembly to buffer the knitted stent jacket from movement of the adjacent element, wherein each of the plurality of buffering element cords has a thickness greater than the knitted stent jacket and an entire length of each of the plurality of buffering element cords overlays the knitted stent jacket, wherein said knitted stent jacket comprises at least three interconnected loops at its distal end, at least one first loop, at least one second loop and at least one third loop; and wherein the assembly comprises at least one separate retainer belt having at least one portion woven through said at least one first loop, past said at least one second loop and through said at least one third loop;

said at least one second loop configured to create a run in said knitted stent jacket upon expansion of said radially expandable stent, wherein the distal end forms a terminal end of the knitted stent jacket and the at least three interconnected loops are arranged circumferentially at the terminal end.

2. The assembly according to claim 1, in which said assembly further comprises at least one run support configured to operatively associate with said created run and prevent at least a portion of said created run from entering said lumen of said radially expandable stent.

3. The assembly according to claim 1, wherein each of the buffering element cords extends the entire length of the knitted stent jacket.

4. An assembly for opening a vessel lumen comprising:
a radially expandable stent configured to open the vessel lumen, said radially expandable stent comprising a curved wall having a proximal portion, a distal portion, and a lumen connecting said proximal portion and said distal portion;
a knitted stent jacket comprising a tubular wall that substantially surrounds an exterior surface of said radially expandable stent; and
a plurality of buffering element cords having an external surface placed against an external surface of said knitted stent jacket, covering only a minor portion of a surface of the knitted stent jacket, in a manner which spaces the knitted stent jacket from an adjacent element of the assembly to buffer the knitted stent jacket from movement of the adjacent element, wherein each of the buffering element cords extends the entire length of the knitted stent jacket and has a thickness greater than the knitted stent jacket and an entire length of each of the plurality of buffering element cords overlays the knitted stent jacket.

5. The assembly according to claim 4, including at least one radiopaque marker on said knitted stent jacket.

6. The assembly according to claim 5, in which said at least one radiopaque marker is located on a proximal portion of said knitted stent jacket.

7. The assembly according to claim 5, in which said at least one radiopaque marker is offset distally from a proximal portion of said knitted stent jacket.

8. The assembly according to claim 5, in which said at least one radiopaque marker is located on a distal portion of said knitted stent jacket.

9. The assembly according to claim 5, in which said at least one radiopaque marker is offset proximally from a distal portion of said knitted stent jacket.

10. The assembly according to claim 4, comprising a compression sheath in which said radially expandable stent is moveably set, said compression sheath including at least one radiopaque marker.

11. The assembly according to claim 10, in which said at least one radiopaque marker is located on a distal portion of said compression sheath.

12. The assembly according to claim 10, in which said at least one radiopaque marker is located proximally to a distal portion of said compression sheath.

13. The assembly according to claim 10, including at least one extension of said compression sheath, said at least one extension being positioned between at least a portion of said knitted stent jacket and at least a portion of said radially expandable stent.

14. The assembly according to claim 10, wherein the plurality of buffering element cords are interposed between the knitted stent jacket and the compression sheath.

15. The assembly according to claim 4, wherein the plurality of buffering element cords are interposed substantially parallel to a longitudinal axis of the lumen of the radially expandable stent.

16. The assembly according to claim 4, in which said knitted stent jacket is designed to resist damage during expansion of the radially expandable stent.

* * * * *